(12) United States Patent
Taylor-Papadimitriou et al.

(10) Patent No.: US 6,222,020 B1
(45) Date of Patent: Apr. 24, 2001

(54) ANTIGENS DERIVED FROM THE CORE PROTEIN OF THE HUMAN MAMMARY EPITHELIAL MUCIN

(75) Inventors: Joyce Taylor-Papadimitriou, Berkhamsted; Sandra Gendler, London; Joy Burchell, Uckfield, all of (GB)

(73) Assignee: Imperial Cancer Research Technology Limited, Croydon (GB)

( * ) Notice: Subject to any disclaimer, the term of this patent is extended or adjusted under 35 U.S.C. 154(b) by 0 days.

(21) Appl. No.: 08/456,919

(22) Filed: Jun. 1, 1995

Related U.S. Application Data

(62) Division of application No. 08/134,992, filed on Oct. 12, 1993, now abandoned, which is a continuation of application No. 07/381,663, filed as application No. PCT/GB88/00011 on Jan. 7, 1988, now abandoned, which is a continuation-in-part of application No. 07/041,306, filed on Apr. 22, 1987, now abandoned.

(30) Foreign Application Priority Data

| Jan. 7, 1987 | (GB) | 8700269 |
| Jan. 7, 1987 | (GB) | 8700279 |
| Nov. 9, 1987 | (GB) | 8726172 |

(51) Int. Cl.⁷ .............................. C07K 14/47; C07K 17/06
(52) U.S. Cl. .................. 530/395; 530/300; 530/328; 530/330; 530/350; 530/388.8
(58) Field of Search .............................. 530/387.7, 388.8, 530/389.7, 300, 350, 365

(56) References Cited

U.S. PATENT DOCUMENTS 4,707,438   11/1987   Keydar .

OTHER PUBLICATIONS

Gendler, S.J. et al.,*Proc. Natl. Acad. Sci., USA* , 84, 6060–6064 (1987).
Gendler, S.J. et al., *Biological Abstracts/RRM*, 32, 49293 (1986) and *Journal of Cell Biology (US)*, 103(5, part 2), 27A (1986).
Gendler, S.J. et al., *J. Biol. Chem.*, 263(26), 12820–12823 (1988).
Maniatis, T. et al., Molecular Cloning: A Laboratory Manual, Coldspring Harbor Laboratory, Cold Spring Harbor, NY (1982).
Reide, J. Mol. Biol 191:255, 1986.*
Cladaras, Virology 140: 28–43, 1985.*
Burchell, J. Immunol. 131:508, 1983.*
Gendler, Breast Cancer Research 1988 p. 112.*
Bio:Critical Syergy: The Biotechnology Industry and Intellectual Property Protection 1994 pp. 74 and 100–107.*

* cited by examiner

Primary Examiner—Nancy A. Johnson
(74) Attorney, Agent, or Firm—Iver P. Cooper

(57) ABSTRACT

Antigens are derived from the tandem repeat sequence of the core protein of a human polymorphic epithelial mucin. These antigens include a core protein epitope which is recognized by certain antibodies which also bind certain carcinoma antigens, but not fully processed HPEM glycoprotein as produced by the normal lactating human mammary gland.

32 Claims, 10 Drawing Sheets

Figure 12:
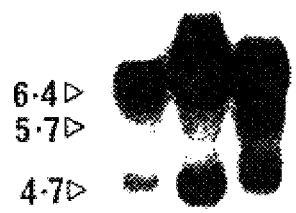

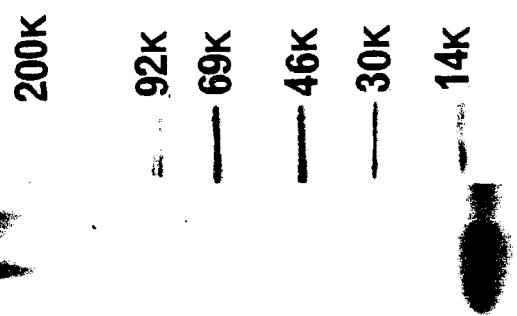
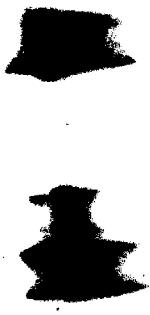
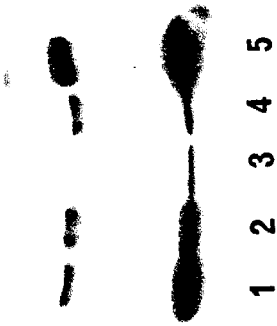

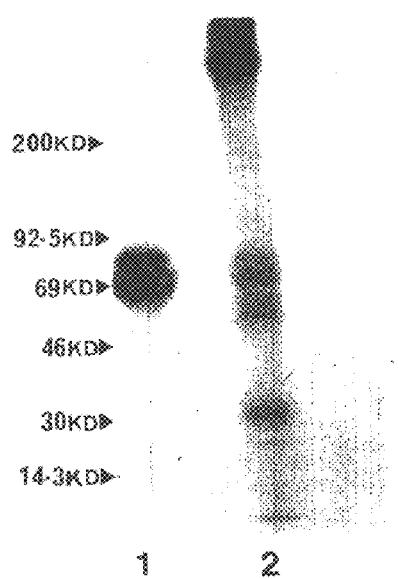
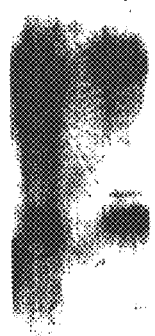
Fig.3.
Fig.4A. Fig.4B. Fig.4C.

Fig.5A.  Fig.5B. 
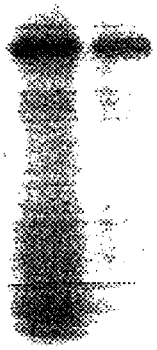

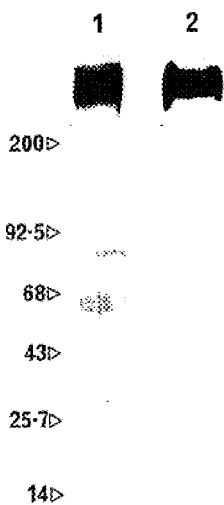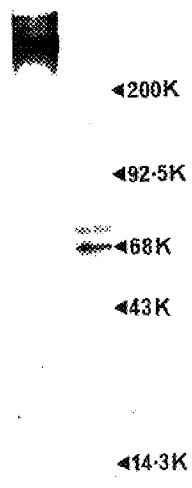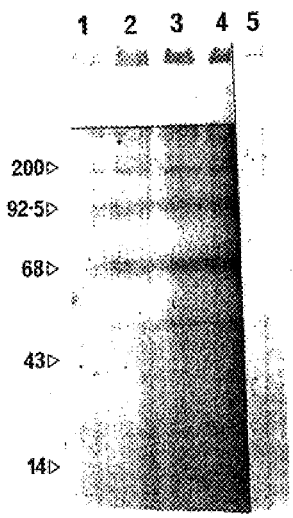

Fig.10.
200 K ▷
92·5 K ▷
3  4  6  7  8  9  10
Fig.11.
2028 bp ▷ 
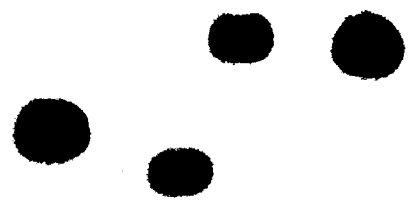
603 bp ▷
310 bp ▷
194 bp ▷
10  9  7  6  8  4  3

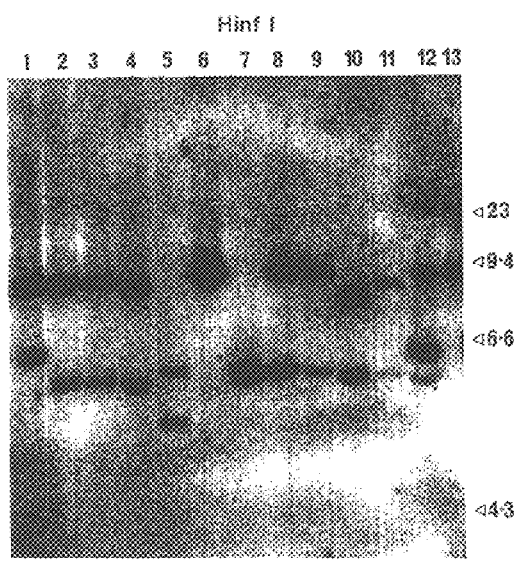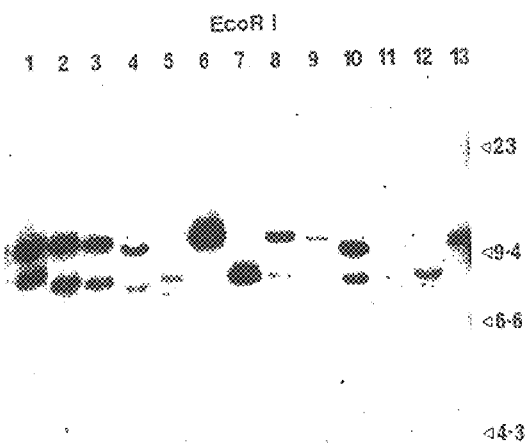

ANTIGENS DERIVED FROM THE CORE PROTEIN OF THE HUMAN MAMMARY EPITHELIAL MUCIN

This application is a division of U.S. Ser. No. 08/134,992, filed Oct. 12, 1993, now abandoned which is a continuation of U.S. Ser. No. 07/381,663, filed Sep. 7, 1989, now abandoned which is the national stage of PCT/GB88/00011, filed Jan. 7, 1988, now abandoned, which is a continuation-in-part of U.S. Ser. No. 07/041,306, filed Apr. 22, 1987, now abandoned, all hereby incorporated by reference.

The present invention relates to DNA probes for detecting a tandemly-repeated nucleotide sequence in the gene encoding mucin glycoprotein expressed by human mammary epithelial cells, to the use of the probe in diagnosis and in "fingerprinting" individuals, to the polypeptides expressed by the corresponding mucin gene, to antibodies against the polypeptides and to the use of the polypeptides and antibodies in the diagnosis and therapeutic treatment of cancer.

Normal and malignant human mammary epithelial cells express high molecular weight glycoproteins (gps) which are extensively glycosylated and very antigenic. As a result, many of the monoclonal antibodies (MAbs) selected for reactivity with human breast cancer and other carcinomas are found to react with molecules which are produced in abundance by the fully differentiated human mammary tissue and are found in the milk fat globule (MFG) and in milk. However, the level of expression of a particular antigenic determinant may be different in the gps produced by the normal differentiated cell and in the similar molecules produced by breast cancers. This means that some antibodies can show a certain specificity for reacting with tumour gps.

The molecules bearing the epitopes recognised by these antibodies are complex and have been difficult to analyse, both because they are large and heavily glycosylated (>250,000 daltons) and because of the complex pattern of expression. Two of the MAbs, HMFG-1 and -2, react with a component in human milk which appears to be greater than 400,000 daltons, whereas the molecules found in sera and tumours are smaller, although the dominant components are still greater then 200,000 daltons on immunoblots. The large glycoprotein produced by the differentiated mammary epithelial cells found in human milk or in the milk fat globule has been purified and shown to have some of the characteristics of the mucins. This component contains a large amount of carbohydrate joined in O-linkage to serine and threonine residues via the linkage sugar N-acetylgalactosamine. Moreover, the core protein contains high levels of serine, threonine and proline and low levels of aromatic and sulphur containing amino acids.

These mucin-like glycoproteins are also secreted by a number of other normal epithelial cells. The monoclonal antibody HMFG-1 is highly reactive with the milk mucin and evidence suggests that the epitope recognised by this antibody is more abundant on the fully processed mucin, characteristic of normal differentiation.

In tumours, the molecular weight of the molecules carrying these antigenic determinants differs among individual tumours and, in the case of the components recognised by the HMFG-2 antibody, can range from 80–400K daltons. Although it appears that the differences observed in the mobility of the high molecular weight bands are due to genetic polymorphism this probably does not explain variations in the size of the lower bands. It has been proposed that these may be the result of aberrant processing occurring in the tumour cell possibly within the glycosylation pathways.

For the majority of the monoclonal antibodies reacting with this group of molecules the exact nature of the antigenic epitopes remains unclear but circumstantial evidence has suggested that carbohydrate may at least be partly involved in many of the epitopes. Moreover, from previously available data it was not known whether the mucin found in the normal differentiated cells, and that observed in the tumours, contain the same core protein, or just carry common carbohydrate determinants.

Mucin has now been isolated from human milk by affinity chromatography enabling identification of the core protein and the gene encoding the protein. This has been found to be a highly polymorphic gene defined by the peanut urinary mucin (PUM) locus [see Swallow et al., *Disease Markers,* 4, 247, (1986) and *Nature,* 327, 82–84 (1987)]. The gene product, which is hereafter referred to as human polymorphic epithelial mucin or HPEM, has been detected in breast tumours and other carcinomas as well as in some normal epithelial tissues.

It has now been found that the HPEM core protein has epitopes which also appear in the aberrantly processed gps produced by adenocarcinoma cells. Certain of these epitopes are not exposed in the fully processed mucin glycoprotein produced by the lactating mammary gland.

In one aspect the present invention therefore provides an antibody against a human mucin core protein which antibody substantially does not react with a fully processed human mucin glycoprotein.

As used herein the term "antibody" is intended to include fragments of antibodies bearing antigen binding sites such as the $F(ab')_2$ fragments.

Antibodies according to the present invention react with HPEM core protein, especially as expressed by colon, lung, ovary and particularly breast carcinomas, but have reduced or no reaction with the corresponding fully processed HPEM. In a particular aspect the antibodies react with HPEM core protein but not with fully processed HPEM glycoprotein as produced by the normal lactating human mammary gland.

Antibodies according to the present invention have no significant reaction with the mucin glycoproteins produced by pregnant or lactating mammary epithelial tissues but react with the mucin proteins expressed by mammary epithelial adenocarcinoma cells. These antibodies show a much reduced reaction with benign breast tumours and are therefore useful in the diagnosis and localisation of breast cancer as well as in therapeutic methods.

The antibodies may be used for other purposes including screening cell cultures for the polypeptide expression product of the human mammary epithelial mucin gene, or fragments thereof, particularly the nascent expression product. In this case the antibodies may conveniently be polyclonal or monoclonal antibodies.

Antibodies according to the present invention may be produced by innoculation of suitable animals with HPEM core protein or a fragment thereof such as the peptides described below. Monoclonal antibodies are produced by the method of Kohler & Milstein (Nature 256, 495–497/1975) by immortalising spleen cells from an animal innoculated with the mucin core protein or a fragment thereof, usually by fusion with an immortal cell line (preferably a myeloma cell line), of the same or a different species as the innoculated animal, followed by the appropriate cloning and screening steps.

In a particular aspect the present invention provides the monoclonal antibodies designated SM3 against the HPEM core protein. In another aspect the invention provides the hybridoma cell line which secretes the antibodies SM3 and has been designated HSM3. Samples of HSM3 have been deposited with ECACC (Public Health Laboratory Service, Centre for Applied Microbiology and Research, ECACC, Porton Down, Salisbury, Wilts, England) on Jan. 7, 1987 under accession number 87010701.

Using antibodies according to the invention it has been possible to screen a phage library constructed from mRNA isolated from a human breast cancer cell line to identify sequences coding for portions of the mucin core protein. Complementary DNA sequences have been constructed and from these it has surprisingly been found that the gene encoding the core protein contains multiple tandem repeats of a 60 base sequence leading to considerable polymorphism sufficiently extensive that cDNA fragments corresponding to the repeat sequence would be useful for fingerprinting DNA. The fingerprinting thus made possible has applications in for instance ascertaining whether bone marrow growth after transplants is from the host or the donor and in forensic medicine for identifying individuals using body tissues or fluids.

Accordingly the present invention also provides a nucleic acid fragment comprising at least 17 nucleotide bases the fragment being hybridisable with at least one of a) the DNA sequence

```
5'                                          *
ACC GTG GGC TGG GGG GGC GGT GGA GCC CGG-

GGC CGG CCT GGT GTC CGG GGC CGA GGT GAC-
                                       *
ACC GTG GGC TGG GGG GGC GGT GGA GCC CGG-
                                      3'
GGC CGG CCT GGT GTC CGG GGC CGA GGT GAC
``` b) DNA complementary to the DNA of a), i.e. of sequence

```
5'
GTC ACC TCG GCC CCG GAC ACC AGG CCG GCC-
 *
CCG GGC TCC ACC GCC CCC CCA GCC CAC GGT-

GTC ACC TCG GCC CCG GAC ACC AGG CCG GCC-
 *                                    3'
CCG GGC TCC ACC GCC CCC CCA GCC CAC GGT
``` c) RNA having a sequence corresponding to the DNA sequence of a) and d) RNA having a sequence corresponding to the complementary DNA sequence of b).

The sequences in (a) and (b) each include a double tandem repeat sequence of 120 bases. Fragments according to the invention may correspond to any portion of this sequence including portions bridging the start point of the repeat.

Fragments according to the invention will hybridise under conditions of low stringency with the DNA and RNA sequences (a) to (d) above. Preferred fragments are those which also hybridise under conditions of high stringency. The most preferred fragments of the invention are those which have sequences exactly identical to, or exactly complementary to the sequences (a) to (d) above.

Normally a given DNA or RNA fragment according to the invention will be capable of hybridising with both DNA according to a) and RNA according to c) or with both DNA according to b) and RNA according to d) above.

Preferably the nucleic acid fragment according to the present invention will comprise a portion of at least 30 nucleotide bases capable of hybridising with at least one of a) to d) above, more preferably at least 50 such bases and most preferably the fragment contains a sequence of 60 bases exactly complementary to one of the repeat sequences of a), b) c) or d) above. Other fragments of the invention may comprise two or more repeats of such a sequence, optionally with minor variations by way of substitution. Preferably such fragments include an integral number of such repeat sequences. Further fragments of the invention comprise the tandem repeat sequence and additional coding or non-coding 5' and/or 3' flanking sequences corresponding to the HPEM gene or a portion thereof.

When the existence of a tandem repeat sequence was first identified it was believed that the sequence consisted of 59 base pairs corresponding with the sequences indicated in (a) and (b) above except for the lack of the base indicated with "*".

Many fragments according to the invention as originally defined in British Patent Application No. 8700269 also conform with the new definition of fragments as set out herein and those fragments of sequences defined under (a), (b), (c) or (d) above which do not include the bases marked "*" form a particular aspect of the present invention. Such fragments have sequences corresponding to at least a portion of the sequences a') GTG GGC TGG GGG GGC GGT GGA GCC a") CGG GGC CGG CCT GGT GTC CGG GGC CGA GGT GAC AC b') DNA complementary to the sequence of a') or a"), c') RNA having a sequence corresponding to the sequence of a') or a") and d') RNA having a sequence corresponding to one of the complementary DNA sequences of b')

In the human genome the DNA tandem repeat sequence comprises antiparallel double stranded DNA, one strand having sequence (a) and being paired with a strand having sequence (b).

As mentioned above the nucleic acid fragments of the invention may be used as a probe for detecting one or other strand of the DNA tandem repeat sequence in the human genome, or RNA transcribed from either strand and hence for identifying the gene or genes for human mucin core proteins, mRNA transcribed therefrom and complementary DNA and RNA. For such purposes it may be convenient to use the complete normal gene comprising at least one tandem repeat sequence, or mRNA transcribed therefrom or to attach non-complementary fragments to either or both 5' and 3' ends of a fragment according to the invention and/or to attach detectable labels (such as radioisotopes, fluorescent or enzyme labels) to the probe or to bind the probe to a solid support. All of these may be achieved by conventional methods and the nucleic acid fragments of the invention may be produced de novo by conventional nucleic acid synthesis techniques.

The nucleic acid fragments of the present invention may also be used in active immunisation techniques. In such methods the fragment codes for a polypeptide chain substantially identical to a portion of the mucin core protein and may be extended at either or both the 5' and 3' ends with further coding or non-coding nucleic acid sequences including regulatory and promoter sequences, marker sequences and splicing or ligating sites. Coding sequences may code for corresponding portions of the mucin core protein chain or for other polypeptide chains. The fragment according to the invention, together with any necessary or desirable flanking sequences is inserted, in an appropriate open reading frame register, into a suitable vector such as a plasmid or a viral genome (for instance vaccinia virus genome) and is then expressed as a polypeptide product by conventional techniques. In one aspect the polypeptide product may be produced by culturing appropriate cells transformed with a vector, harvested and used as an immunogen to induce active immunity against the mucin core protein. In another aspect the vector, particularly in the form of a virus, may be directly innoculated into a human or animal to be immunised. The vector then directs expression of the polypeptide in vivo and this in turn serves as an immunogen to induce active immunity against the mucin core protein.

The invention therefore provides nucleic acid fragments as hereinbefore defined for use in methods of treatment of the human or animal body by surgery or therapy and in diagnostic methods practised on the human or animal body. The invention also provides such methods for treatment of the human or animal body by surgery or therapy and diagnostic methods practised in vivo as well as ex vivo and in vitro.

The invention further provides a polypeptide comprising a series of residues encoded by the DNA tandem repeat sequence, the sequence shown at (b) above being the coding sequence. Polypeptides according to the invention are selected from any of those having 5 or more amino acid residues represented by the following amino acid sequence

```
Val Thr Ser Ala Pro Asp Thr Arg Pro Ala Pro Gly Ser Thr

Ala Pro Pro Ala His Gly*Val Thr Ser Ala Pro Asp Thr Arg

Pro Ala Pro Gly Ser Thr Ala Pro Pro Ala His Gly ("*" marks the start of the repeat in the peptide).
```

Polypeptides according to the invention may have a sequence corresponding with any portion of the 40 residue sequence above and may include the start point of the repeat sequence.

Other polypeptides according to the invention include three or more repeats of the 20 amino acid repeat sequence. Such polypeptides may include minor variations by way of substitution of individual amino acid residues.

The invention further provides polypeptides as defined above modified by addition of N-acetyl galactosamine (a linkage sugar) or serine and/or threonine residues and by addition of oligosaccharide moieties to that or via other linkage sugars and/or fragments linked to carrier proteins such as keyhole limpet haemocyanin, albumen or thyroglobulin.

Preferably the polypeptide comprises at least 10 amino acid residues of the sequence above, more preferably 20 residues. The polypeptide may comprise the full sequence above. Such polypeptides may further comprise additional amino acid residues, preferably conforming to the amino acid sequence of HPEM core protein.

In a further aspect the present invention provides the HPEM core protein. This is encoded by the PUM gene and may be produced by recombinant DNA techniques and expressed without glycosylation in human or non-human cells. Alternatively it may be obtained by stripping carbohydrate from native human mucin glycoprotein which itself may be produced by isolation from samples of human tissue or body fluids or by expression and full processing in a human cell line. The HPEM core protein may be used for raising antibodies in animals for use in passive immunisation, diagnostic tests and tumour localisation and in active immunisation of humans.

The invention further provides antibodies (monoclonal or polyclonal), and fragments thereof, against any of the polypeptides described above. Such antibodies may be obtained by conventional methods and are useful in diagnostic and therapeutic applications.

The invention further provides antibodies (monoclonal or polyclonal), or fragments thereof, linked to therapeutically or diagnostically effective ligands. For therapeutic use of the antibodies the ligands are lethal agents to be delivered to cancerous breast or other tissue in order to incapacitate to kill transformed cells. Lethal agents include toxins, radioisotopes and 'direct killing agents' such as components of complement as well as cytotoxic or other drugs. Further therapeutic uses of the antibodies inclusive passive immunisation.

The invention further provides therapeutic methods comprising the administration of effective non-toxic amounts of such antibodies or fragments thereof and antibodies or fragments thereof for use in therapeutic treatment of the human or animal body. Especially in therapeutic applications it may be appropriate to modify the antibody by coupling the Fab region thereof to the Fc region of antibodies derived from the species to be treated (e.g. such that the Fab region of mouse monoclonal antibodies may be administered with a human Fc region to avoid immune response by a human patient) or in order to vary the isotype of the antibody.

In the diagnostic field the antibodies may be linked to ligands such as solid supports and detectable labels such as enzyme labels, chromophores and fluorophores as well as radioisotopes and other directly or indirectly detectable labels. Preferably monoclonal antibodies or fragments thereof are used in diagnosis.

The invention further provides a diagnostic assay method comprising contacting a sample suspected to contain abnormal human mucin glycoproteins with an antibody as defined above. Such methods include tumour localisation involving administration to the patient of the antibody or fragment thereof bearing a detectable label or of an antibody or fragment thereof and, separately simultaneously or sequentially in either order a labelling entity capable of selectively binding the antibody or fragment thereof. The invention also provides antibodies or fragments thereof for use in diagnostic methods practised on the human or animal body.

Particular uses of the antibodies include diagnostic assays for detecting and/or assessing the severity of breast, ovary and lung cancers.

Diagnostic test kits are provided for use in diagnostic assays and comprise antibody or a fragment thereof, optionally suitable labels and other reagents and, especially for use in competitive assays, standard sera.

The invention will now be illustrated by the following Examples and with reference to the figures of the accompanying drawings in which

FIGURE LEGENDS

FIG. 1: Purification of the milk mucin by immunoaffinity chromatography using the antibody HMFG-1. Milks from several individuals were combined and absorbed to a HMFG-1-Sepharose column as described in Methods. The material eluting at low pH was iodinated and subjected to PAGE electrophoresis and autoradiography (track 1). The iodinated material was precipitated using the Protein A method with antibodies HMFG-1 (track 5), HMFG-2 (track 2), ST254 (track 3) and RPMI+20% FCS (track 4).

FIGS. 2A–2B: Comparison of the $^{125}$I labelled purified milk mucin with immunoblot of human skimmed milk. FIG. 2A: human skimmed milk was subjected to SDS polyacrylamide electrophoresis, transferred to nitrocellulose paper, the blot probed with the monoclonal antibody HMFG-1 and binding detected using an ELISA method. FIG. 2B: after purification on an HMFG-1 affinity column followed by G75 Sephadex chromatography the milk mucin was iodinated by the Bolton and Hunter method and subjected to SDS polyacrylamide electrophoresis and autoradiography.

FIG. 3: Autoradiography of the iodinated milk mucin after treatment with hydrogen fluoride. The purified milk mucin was treated with HF for 3 hours at room temperature (track 1) or 1 hour at 4° C. (track 2) and the resulting preparations were then iodinated and run on SDS polyacrylamide gels.

FIGS. 4A–4C: Reactivity of the intact, partially stripped or extensively stripped milk mucin with iodinated lectins. The purified intact milk mucin (track 1), the mucin treated with HF for 1 hour at 4° C. (track 2) and the mucin treated for 3 hours at room temperature (track 3) were subjected to SDS polyacrylamide electrophoresis and then transferred to nitrocellulose paper. The paper was then probed with $^{125}$I PNA (peanut agglutinin (FIG. 4A)), $^{125}$I WGA (wheat germ agglutinin (FIG. 4B)), or $^{125}$I HPA (Helix pomatia agglutinin (FIG. 4C)).

FIGS. 5A–5B: Immunoprecipitation and immunoblots of the partially and extensively stripped mucin. FIG. 5A: the $^{125}$I extensively stripped mucin was immunoprecipitated with SM-3 (track 3), HMFG-2 (track 2) or NS2 medium as a control (track 1) by the protein A plate method (see Materials and Methods). FIG. 5B: the partially stripped mucin (track 1) or extensively stripped mucin (track 2) was run on SDS polyacrylamide gels and transferred to nitrocellulose paper. The blot was then reacted with a cocktail of SM-3 and SM-4 monoclonal antibodies and the binding detected using an ELISA method.

Figure 6A:
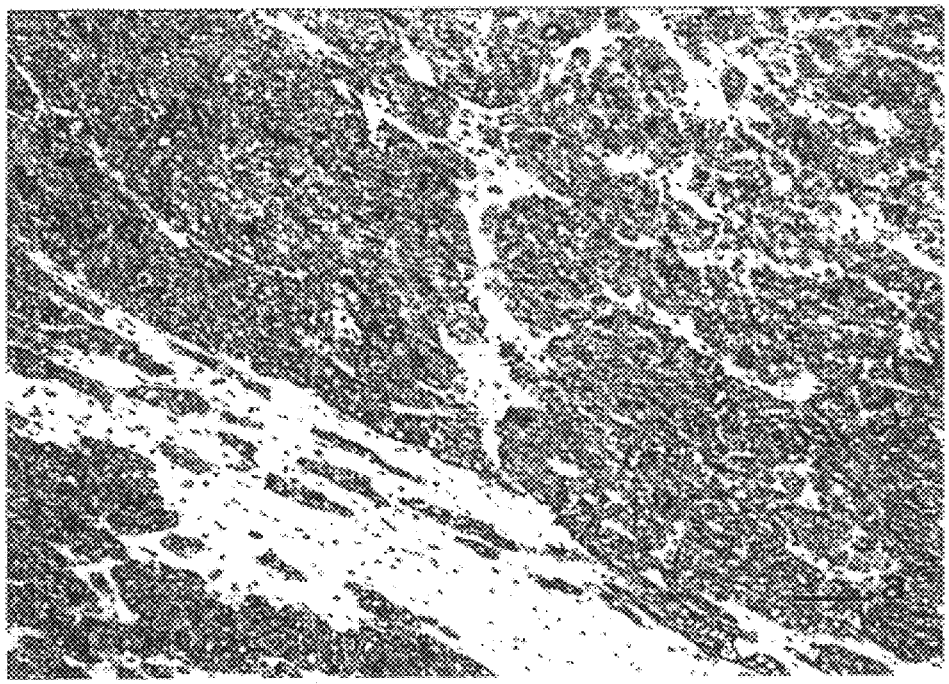
Figure 6B:
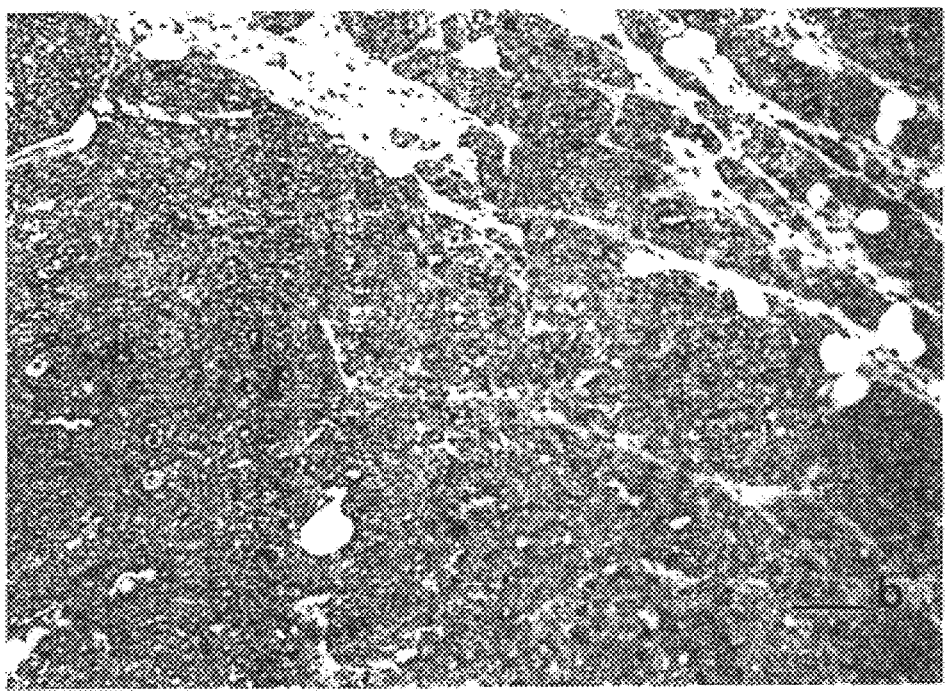
Figure 6C:
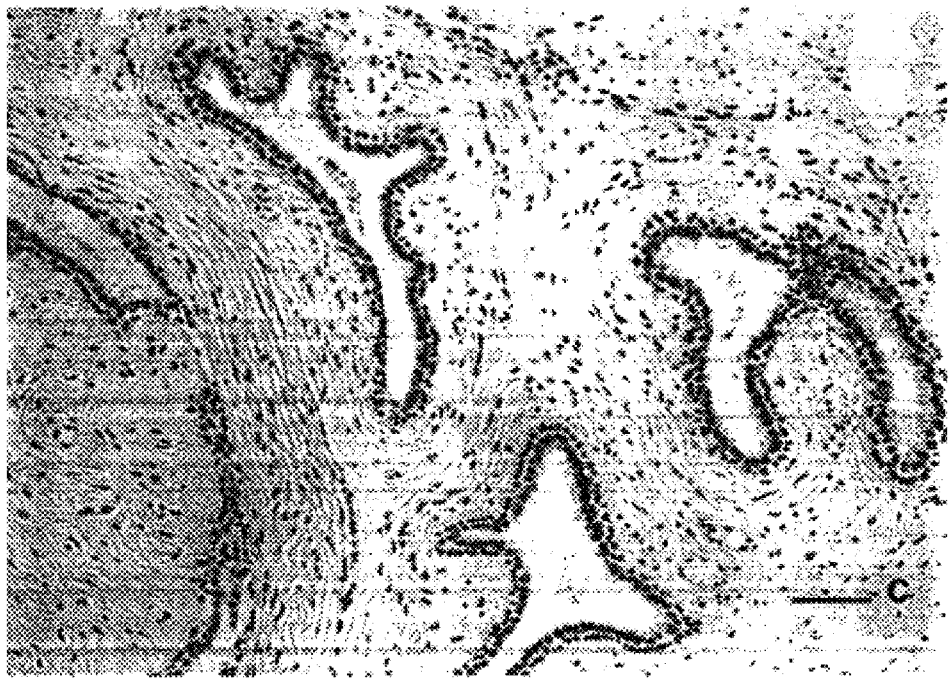
Figure 6D:
Figure 6E:
Figure 6F:
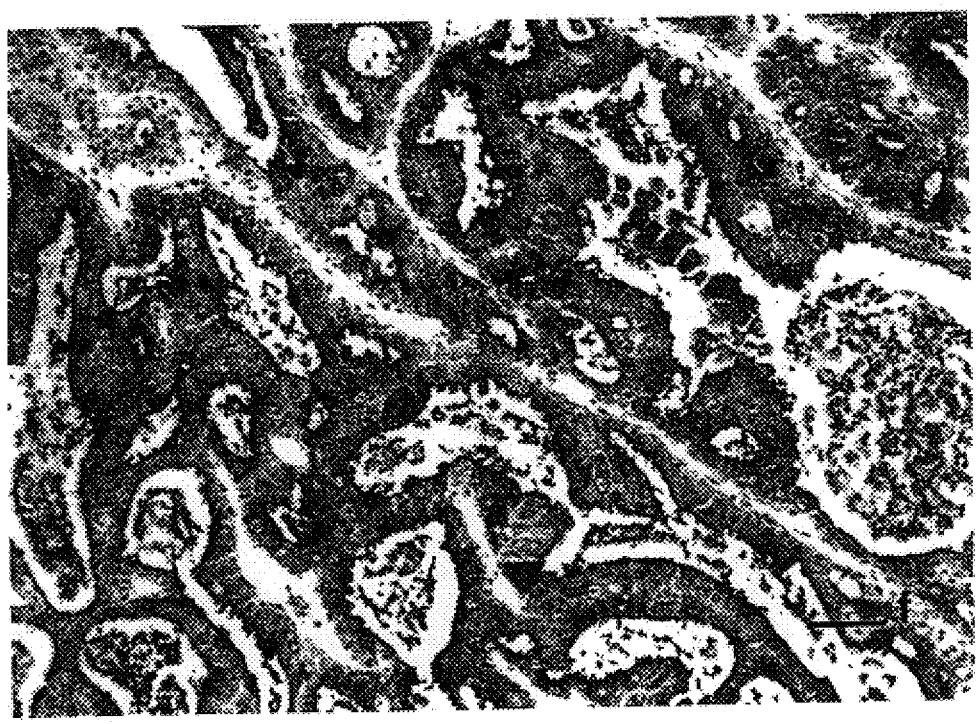
Figure 6G:
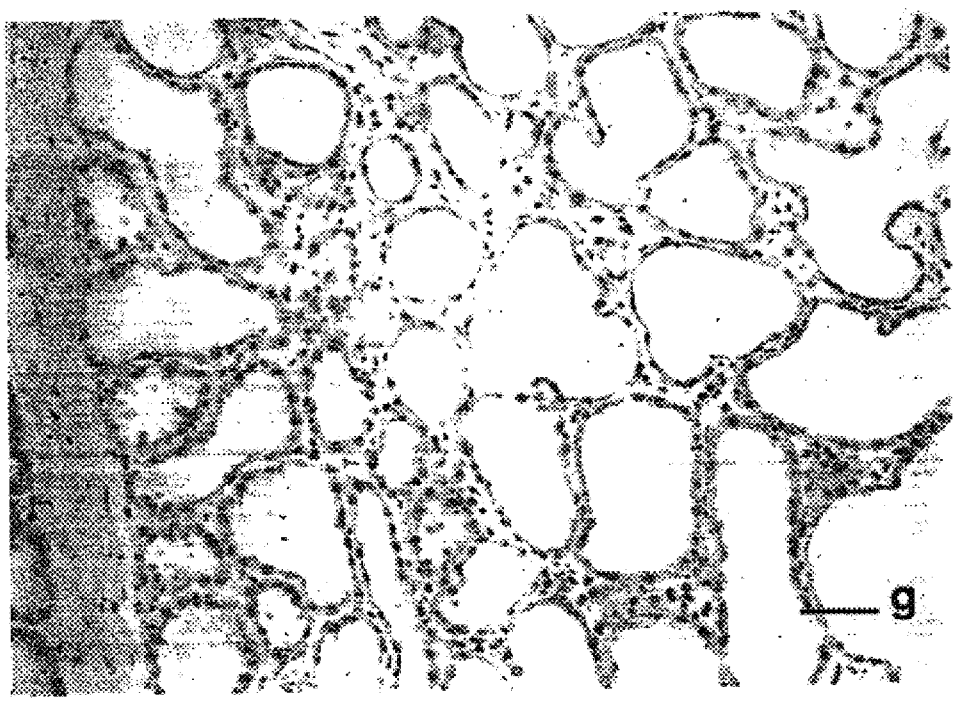
Figure 6H:
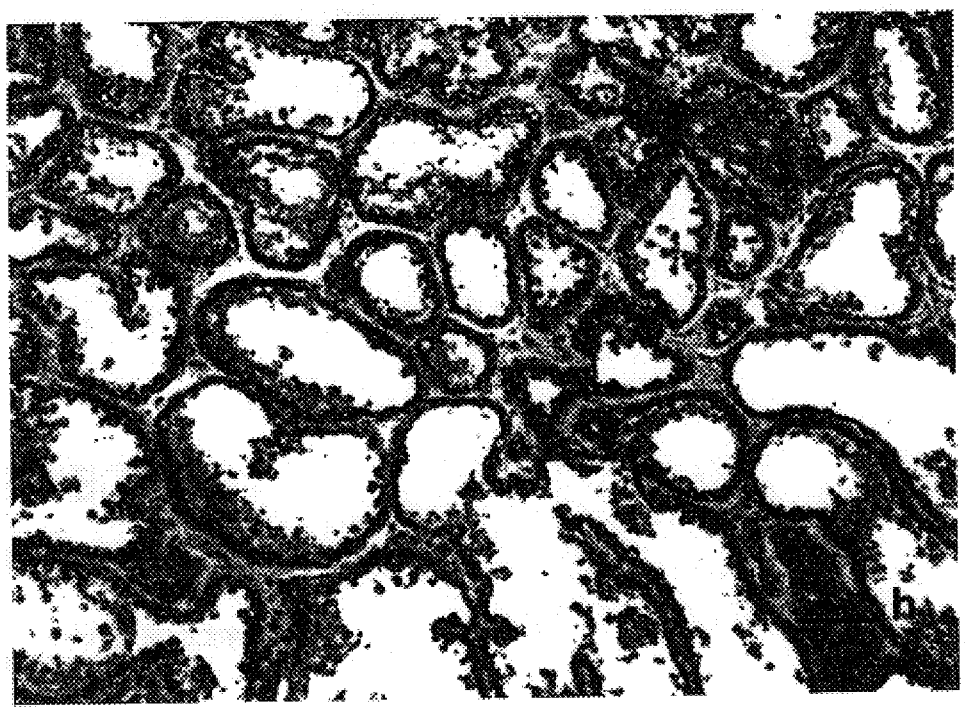

FIGS. 6A–6H: Reactivity of monoclonal antibodies SM-3 and HMFG-2 with methacarn fixed breast tissue and tumour sections using an indirect immunoperoxidase staining method. Infiltrating ductal carcinoma showing strong reactivity with both SM-3 (FIG. 6A) and HMFG-2 (FIG. 6B). Fibroadenoma showing no reactivity with SM-3 (FIG. 6C) and strong heterogeneous staining of the epithelium wiht HMFG-2 (FIG. 6D). Papilloma showing very weak reactivity with SM-3 (FIG. 6E) and strong positivity with HMFG-2 (FIG. 6F). Both normal resting breast (FIG. 6G) and lactating breast were negative when stained with SM-3, whereas both tissues stained positively with HMFG-2 with lactating breast must stronger than normal resting breast (FIG. 6H).

FIGURE LEGENDS

FIG. 7. Periodic acid-silver stained milk mucin after antibody affinity column and gel filtration column. Milk mucin was purified on and HMFG-1 antibody affinity column (lane 1) followed by passage through a G75 Sephadex column (lane 2), subjected to NaDodSO$_4$/polyacrylamide gel electrophoresis, and silver stained following treatment of gels with 0.2% periodic acid.

FIG. 8. Silver stain of partially and totally stripped core protein from milk mucin. The purified milk mucin was deglycosylated by treatment with anhydrous hydrogen fluoride for 1 hr at 0° C. (lane 1) and 3 hr at room temperature (lane 2), separated by electrophoresis through a NaDodSO$_4$/polyacrylamide gel (10%) and silver stained.

FIG. 9. Immunoprecipitation with MAbs of in vitro translated protein products from MCF-7 poly(A)$^+$ RNA. Poly(A)$^+$ RNA from MCF-7 cells was translated in a rabbit reticulocyte lysate system (Amersham) in the presence of [$^{35}$S]methionine (1000 Ci/mmole; 1Ci=37 GBq) following the manufacturer's conditions. Samples containing 5×10$^4$ acid precipitable cpm were precipitated with MAba SW-4 (lane 1), SM-3 (lane 2), HMFG-2 (lane 3), HMFG-1 (lane 4) and an irrelevant MAb to interferon (lane 5, 24), separated on a NaDodSO$_4$/polyacrylamide gel (10%), impregnated with Amplify and exposed to IAR-5 film at −70° C. for 20 days.

FIG. 10. Immunoblot analysis of fusion proteins from the λmuc clones. The phage clones λMUC 3, 4, 6, 7, 8, 9 and 10 were used to lysogenize bacterial strain Y 1089. Lysogens were grown at 32° C., shifted to 42° C., and then induced with IPTG. Lysogen proteins were fractionated by electrophoresis through a NaDodSO$_4$/polyacrylamide gel (7.5%), transferred to nitrocellulose, and reached with HMFG-2. The binding was detected with an ELISA method using 4-chloro-1-naphthol as the substrate. The numbers are those of the λ clones.

FIG. 11. Hybridization of pMUC10 to cDNA inserts of pMUC clones. DNA from the plasmid clones was digested with restriction enzyme EcoRI to excise the cDNA inserts, separated by electrophoresis on 1.4% agarose and transferred to Biodyne nylon membrane. The filter was hybridized using standard conditions (34) to the insert from pMUC10 which was labelled with [α-$^{32}$p]dCTP by the method of random priming (41). Lanes: plasmid clones 3,4,6,7,8,9,10.

FIG. 12. RNA blot hybridization analysis of mammary breast mucin mRNA. 10 μg of total RNA from human breast cancer cells MCF-7 (lane 1) and T47D (lane 2), normal human mammary epithelial cells HuME (lane 3), human embryonic fibroblasts ICRF 23 (lane 4), Daudi cells (lane 5) and carcinosarcoma HS578T cells (lane 6) were separated in a 1.3% agarose/glyoxal gel, blotted on to nitrocellulose and hybridized to the pMUC10 EcoRI insert which was labelled with [α-$^{32}$p]dCTP by the method of random priming (41). The size markers were 28S (5.4 kb) and 18S (2.1 kb) rRNAs.

FIGS. 13A and 13B. Polymorphic human DNA fragments detected by hybridization with pMUC10 probe. Genomic DNA samples prepared from the white blood cells from ten individuals (six unrelated) and from three cell lines were digested to completion with HinfI and EcoRI, fractionated by electrphoresis through 0.7% and 0.6% agarose, respectively, and transferred to Biodyne nylon membranes. The filter was hybridized to the pMUC10 DNA insert which was labelled with [α$^{32}$p]dCTP by the method of random priming (41). X-ray film was exposed for 1 day at −70° C. with intensifying screens. Lanes 1–4 father, two daughters and mother, lanes 5–10 unrelated individuals, lane 11 is MCF-7, lane 12 is ZR75-1, lane 13 is ICRF-23. The DNA samples exhibit a wide distribution of sizes. Numbers indicate length of DNA in kb. The apparent bands at 23 Kb are in lanes 12 and 13 are artefacts introduced in autoradiography

EXAMPLE 1

Purification of the milk mucin

The milk mucin was purified from human skimmed milk by passage through an HMFG-1 affinity column followed by size exclusion chromatography. The HMFG-1 monoclonal antibody was purified from tissue culture supernatant using a protein A column (1). The purified antibody was coupled to cyanogen bromide activated sepharose (Pharmacia) as described in the manufacturer's instructions. Human skimmed milk was passed in batches of 100 ml through the antibody column followed by extensive washing with PBS. Bound antigen was eluted from the column using 0.1M glycine pH 2.5 and the fractions registering an optical density at 260 nm were pooled, dialysed against 0.25M acetic acid and lyophilized. Batches of about 20 mgs were dissolved in 0.25M acetic acid and passed through a G75 Sephadex column (1×100 cm) which had been previously equiligrated with acetic acid. The column was washed with 0.25M acetic acid and 1 ml fractions collected. The peak fractions which were eluted in the void volume were pooled, lyophilized and the dry powder stored at 4° C. Amino acid analysis was performed using a Beckman 6300 amino acid analyser.

Deglycosylation of the milk mucin

To remove the O-linked carbohydrate from the milk mucin the molecule was treated with anhydrous hydrogen fluoride as described by Mort and Lamport (21), and either 1 hour at 4° C. which produced a partially stripped preparation, or 3 hours at room temperature which produced the extensively stripped mucin.

Iodination of the milk mucin

Iodinations of the purified mucin, the partially or extensively stripped mucin were carried out using the Bolton and Hunter method (51). Briefly, the mucin, 2.5 $\mu$g in 20 $\mu$l 0.1M borate buffer pH 8.5, was added to the dried Bolton and Hunter reagent (1 xCi, Amersham International plc) and incubated at room temperature for 15 minutes. The reaction was stopped by the addition of 0.5 ml of 0.2M glycine in borate buffer and after a further 15 minutes incubation, free Bolton and Hunter reagent was removed by passage through a G25 Sephadex column (PD10 columns, Pharmacia) previusly equilibriated in PBS.

Iodination of Lectins

Wheat germ agglutinin (WGA), peanut agglutinin (PNA) (Vector Labs) and Helix pomatia agglutinin (HPA) (Boehringer) were iodinated as described by Karlsson et al. (52) using the chloramine T method.

Polyacrylamide gels and Western blots

Polyacrylamide gel electrophoresis and immunoblotting was performed as described previusly (1). Briefly, samples were run on 5–15% polyacrylamide gels and then electrophoretically transferred to nitrocellulose paper (Schleicher and Schuell) at 50 volts overnight at 4° C. (36). In the immunoblotting experiments the paper was reacted with monoclonal antibodies and binding detected with an ELISA method using 4-chloro-1-naphthol as the substrate. For lectin binding studies the Western blots were reacted with the iodinated lectins as described by Swallow et al. (48).

Production of monoclonal antibodies

A female BALB/c mouse was immunized with 5 $\mu$g of the partially stripped milk mucin in Freund's complete adjuvant and 3 months later boosted with a further 5 $\mu$g of the same preparation in Freund's incomplete adjuvant. After a further 20 days, 5 $\mu$g of the mucin extensively stripped of its carbohydrate was given intravenously in saline solution. The spleen was removed 4 days later, and fused with the NS2 mouse myeloma cell line (53).

Screening of hybridoma supernatant and immunoprecipitations

The screening assay was a modification of that described by Melero and Gonzalez-Rodriguez (54). Multiwell plates were coated with 50 $\mu$l of 0.1 mg/ml protein A (Pharmacia Fine Chemicals) in PBS and allowed to dry overnight at 37° C. The plates were blocked with 5% BSA for 1 hour at 37° C. followed by the addition of 50 $\mu$l of rabbit anti-mouse immunoglobulin (DAK0, diluted with 1:10 in PBS/BSA= PBS/BSA). After incubating for 2 hours at 37° C. The plates were washed twice with PBS containing 1% BSA and 50 $\mu$l of hybridoma supernatant added. The plates were incubated overnight at 4° C., washed twice with PBS/BSA and 50 $\mu$l of iodinated partially stripped mucin containing 100,000 cpm added to each well. The plates were then incubated at room temperature for 4 hours, washed 4 times with PBS/ BSA and the individual wells counted in a gamma counter. For immunoprecipitation experiments 50 $\mu$l of SDS sample buffer containing dithiothreitol was added to each of the wells which were then boiled for 3 minutes and the buffer loaded onto 5–15% polyacrylamide gradient gels.

Staining of tissue sections

Tissues from primary mammary carcinomas, benign breast biopsies, normal breast, and pregnant lactating breast tissue were fixed in methacarn (methanol chloroform and acetic acid 60:30:10) and embedded into paraffin wax. Sections were stained with the antibodies using the indirect peroxidase anti peroxidase method as previously described (47).

Results

Purification of the milk mucin

The milk mucin was purified from human skimmed milk on an HMFG-1 antibody affinity column. Iodination of the eluted material revealed the presence of a large molecular weight component and a 68 KD band. Precipitation of the affinity purified material with antibodies HMFG-1 and HMFG-2 (tracks 2 and 5) followed by gel electrophoresis showed that both the high molecular weight components and the 68 KD component were precipitated by both antibodies (less effectively by HMFG-2). Since the 68 KD component was also precipitated by two unrelated antibodies (FIG. 1, tracks 3 and 4) and this component was not evident on an immunoblot of the purified material reacted with HMFG-1 (FIG. 2A), the 68K component was removed by molecular sieve chromatography on a G75 column. The final purified product showed a major high molecular weight band, with only a trace of the 68K component and a minor contaminant around 14K (FIG. 2B).

A high molecular weight glycoprotein (PAS-0) containing more than 50% carbohydrate in 0-linkage has been purified from the human milk fat globule by Shimiru and Yamauchi (8). To see whether this component was similar to the mucin isolated from milk by affinity chromatography on an HMFG-1 affinity column, the amino acid composition of the purified HMFG-1 reactive mucin was determined and compared to the amino acid composition of the purified PAS-0 component. Table 1 shows that there is good correspondence between the two sets of data, indicating that the core proteins of PAS-0 and the mucin purified here are the same.

Isolation of the core protein of the milk mucin

As there are no enzymes easily available that are efficient at removing 0-linked sugars, and $\beta$ elimination often results in damage to the protein core, the oligosaccharides were removed by treatment of the mucin with anhydrous hydrogen fluoride. This treatment has been shown by Mort and Lamport (21) to be effective in removing sugars from pig submaxillary mucin without damaging the protein core. Amino acid analysis of the material produced after HF treatment of the milk mucin suggested that the protein core was also in this case undamaged, since the composition was the same as that seen in the intact mucin (Table 1).

Initially the milk mucin was exposed to HF for only 1 hour at 4°, but analysis of the product showed that there was only partial removal of the sugars with such treatment, and it was necessary to treat the mucin at room temperature for 3 hours to obtain a molecule which showed no lectin binding ability. FIG. 3 shows an autoradiograph of the iodinated products after treatment for 1 hour at 4° (track 2) or 3 hours at RT (track 1). It can be see from FIG. 3 that the milder treatment results in a mixture of products made up of high molecular weight material which is slightly smaller than the intact mucin and a number of smaller bands. After longer exposure to HF at room temperature, the high molecular weight bands disappeared resulting in polypeptide bands of about 68 KD and 72 KD.

To test for the presence of sugars on the intact mucin and on the products produced after the two different HF treatments each preparation was subjected to acrylamide gel electrophoresis, transferred to nitrocellulose paper and reacted with $^{125}$I-labelled lectins. The lectins used were peanut lectin (PNA) which reacts with galactose linked to N-acetyl galactosamine, wheat germ (WGA) reactive with N-acetyl glucosamine and Helix pomatia agglutinin (HPA) which reacts with the linkage sugar in 0-linked glycosylation, N-acetylgalactosamine. FIGS. 4A–4C show autoradiographs of the reacted blots, and it can be seen that while treatment with HF for 1 hour at 4° (track 2) alters the lectin reactivity of the mucin, carbohydrate is still present. Interestingly, however, there is a much lower level of binding of PNA to the high molecular weight material of the partially stripped mucin than is seen with the intact mucin (track 1). Moreover, this loss in PNA binding ability is accompanied by binding of the linkage sugar specific lectin HPA. This lectin shows no binding at all to the intact mucin, and the changed pattern of lectin binding after limited treatment with HF indicates that sugars masking the 0-linked N-acetylgalactosamine have been stripped off. The smaller component seen in both the intact mucin (track 1) and in the partially stripped preparation (track 2) is a glycoprotein which reacts with WGA, although not with PNA. This may correspond to the component of similar molecular weight (around 68 I) seen after affinity chromatography of the mucin and may represent an intermediate precursor molecule.

FIGS. 4A–4C show clearly that the 68 I and 72K components produced after extensive treatment with HF (3 hr at RT), show no reactivity with the lectins (track 5), including the K-acetylgalactosamine specific lectin HPA. This observation constitutes strong evidence that the sugars have been removed from at least the majority of the molecules, and we will refer to this preparation as the extensively stripped mucin.

Generation of monoclonal antibodies to the milk mucin core protein

A fusion was carried out using the spleen of a mouse that had been immunized with two injections of the partially stripped milk mucin followed by a boost with the extensively stripped mucin. The clones were initially screened against the $^{125}$I partially stripped material using protein A plates (see Methods). Four hybridomas were selected and cloned, and table 2 shows their spectrum of reactivity with the intact, partially and extensively stripped mucin. As can be seen from this table three of the hybridomas which were isolated showed a strong reaction with the partially and extensively stripped mucin and did not react with the intact mucin. These appeared to be good candidates for monoclonal antibodies to the protein core and two, SM-3 and SM-4, were selected to be characterised further.

The monoclonal antibody SM-3 is produced by hybridoma cell line HSM3. HSM3 was deposited under the Budapest Treaty, on Jan. 7, 1987, as accession ECACC 87010701, with the European Collection of Animal Cell Cultures, (now known as the European Collection of Cell Structures), Public Health Laboratory Service, Centre for Applied Microbiology and Research, Porton Down, Salisbury, Wiltshire, United Kingdom. Upon issuance of a U.S. patent, the deposited biological material will be irrevocably and without restriction or condition made available to the public. The release of the deposit does not constitute a license to practice the claimed invention.

It can also be seen from table 2 that the HMFG-1 and HMFG-2 antibodies reacted very strongly with the mucin stripped of its carbohydrate. These two antibodies were, in fact, developed using the intact mucin (from the milk fat globule) as immunogen and, in the case of HMFG-2, growing mammary epithelial cells (14). Their reaction with the stripped mucin was unexpected, as circumstantial evidence had previously led to the belief that carbohydrate might form at lest part of their antigenic epitopes.

Molecular Weight of molecules carrying antigenic determinants

The antibody SM-3 was shown to be of the IgG1 subclass, while the SM-4 antibody was found to be IgM. We therefore chose to use the SM-3 antibody in subsequent experiments since antibodies of the IgM class can present problems in some application. Immunoprecipitation of the extensively stripped material with SM-3 showed a reaction with the lectin unreactive 68K component (FIG. 5A, track 3). The monoclonal antibody HMFG-2 can also be seen to immune precipitate the lectin-unreactive 68K component (track 2). The antibodies were reactive with antigen on immunoblots and FIG. 5B shows the reaction of antibody SM-3 with the dominant 68K band of the extensively stripped mucin (track 2).

We have previously shown that the molecular weight of the components in breast cancer cells carrying determinants found on the milk mucin is lower than 400K and can vary from one tumour to another (1). Reaction of antibody SM-3 with Western blots of gel separated extracts of breast tumour cells shows that this antibody reacts with components of similar molecular weight to those reactive with antibody HMFG-2 (data not shown). Because the antibody SM-3 differs from the antibodies HMFG-1 and 2 in that it does not react with the intact mucin processed by the lactating gland and yet reacts with molecules processed by breast cancer cells, it was appropriate to examine the reaction of SM-3 with a range of breast cancers.

Reactivity of SM-3 with breast tissues and tumours the antibody SM-3 reacted with paraffin embedded tissues provided these were fixed in methacarn (not formal saline). Using this method for preparation of tissue sections, the reaction of the antibody was compared to that of HMFG-2 on breast tissues and tumours with an indirect immunoperoxidase staining method. This analysis showed a dramatic difference in the staining pattern of SM-3 compared to that seen with HMFG-2. Thus, although a strong positive reaction was seen in 20/22 breast cancers stained with SM-3 (as compared to 22/22 stained with HMFG-2), normal resting breast, pregnant or lactating tissues and most benign lesions were largely unstained with SM-3 but were stained with HMFG-2. Some examples of staining patterns of breast tissues and tumours are illustrated in FIGS. 6A–6H.

Twenty-two primary carcinomas and fourteen benign lesions were examined and the reaction of SM-3 compared to the staining with HMFG-2 in each case. In the primary carcinomas, staining with SM-3 was heterogeneous but generally quite strong and always confined to tumour cells; connective tissue and stroma showed no reaction (see FIGS. 6A,B). In the four fibroadenomas examined, staining of the epithelium with HMFG-2 was strong although heterogeneous. In comparison, staining with SM-3 was negative in one case and in the three others staining was confined to only one or two glandular elements. HMFG-2 showed strong positivity on the five papillomas and five cases of cystic disease studied while the staining observed with SM-3 was very much weaker and more heterogeneous (FIGS. 6G,H). The papillomas as a group showed the strongest staining with SM-3, and it can be seen that the staining was membranous or extracellular.

In contrast to HMFG-1 and HMFG-2 which strongly stain lactating and pregnant breast, SM-3 was totally negative with three out of six cases of pregnant or lactating breast (see FIGS. 6C and D). Two positive cases showed only very weak staining of an occasional cell and in the third, staining was confined to two areas of one lobule. Again, in contrast to HMFG-1 and HMFG-2 which do react with some terminal ductal lobular units of normal, resting breast (albeit weakly), SM-3 was totally negative on eight out of the thirteen cases tested and in the other five cases staining was extremely weak and often confined to one or two acini in the tissue section (see FIGS. 6E and F). It should perhaps be noted that the intensity of staining with HMFG-2 seen with normal breast tissues and benign lesions fixed in methacarn was somewhat higher than that reported previously using formalin fixed material (50, 47).

SM-3 was also shown to be negative on sections of normal liver, lung, thymus, sweat gland, epididymus, prostate, bladder, small intestine, large intestine, appendix, thyroid and skin. The antibody showed weak positive staining only with the distal tubules of the kidney, the occasional chief cell of the stomach, the occasional duct cell of the salivary gland and the sebaceous gland.

Discussion

Large molecular weight mucin molecules are expressed by many carcinomas and carry many of the tumour associated antigenic determinants recognised by monoclonal antibodies. These epitopes may also be expressed by some normal epithelium, and some monoclonal antibodies like HMFG-1 react particularly well with a mucin found in normal human milk (1, 17). As long as the study of the mucins is restricted to their detection with antibodies reactive with undefined epitopes, the knowledge of their structure, expression and processing will also be restricted. We have begun to investigate the structure and expression of the mammary mucin by isolating the core protein and developing antibodies which have allowed us to select partial cDNA clones for the gene coding for the core protein. This Example describes the production and characterization of these antibodies.

Treatment of the HMFG-1 affinity purified milk mucin with hydrogen fluoride resulted in the appearance of a dominant band of about 68K daltons and a minor species of about 72 KD on SDS acrylamide gels. These bands showed no reactivity with lectins, including Helix pomatia agglutinin which is specific for N-acetyl galactosamine, the first sugar in 0-linked glycosylation (55). It therefore seems probable that this 68K dalton polypeptide represents the core protein of the mucin. Supportive evidence for this comes from the observation that the antibodies described here, which are reactive with the stripped 68 K component, can precipitate a molecule of this size from the in vitro translation products of mRNA isolated from breast cancer cells expressing the mucin.

As the milk mucin contains at least 50% carbohydrate (16), a protein core of only 68 KD appears too small if the intact molecule has an observed molecular weight greater than 400 KD. However, mucins can be composed of small subunits which aggregate and are held together by some form of non-covalent interactions, as yet not understood. For example, although the molecular weight of the ovine submaxillary mucin has been reported to be greater than $1 \times 10^6$ daltons (45), it has a protein core of only 650 amino acids with a molecular weight of 58,300 daltons (46).

An unexpected finding was that the antibodies HMFG-1 and HMFG-2 which react with the milk mucin, also show a positive reaction with the extensively stripped material which showed no lectin binding capability. Previous indirect evidence, including the resistance to fixation, boiling and reduction, the repetitive nature of their epitopes and the appearance of several bands on immunoblots, had led to the belief that carbohydrate present on the milk mucin was involved in these epitopes. This idea was reinforced by the observation that lectins could block the binding of HMFG-1 and 2 (1). While it is not possible to exclude the possibility that some sugars, undetected by the lectin binding experiments, remain on the extensively stripped mucin described here, this is unlikely to be the explanation for the reactivity of the antibodies HMFG-1 and 2. This can be said since both antibodies have recently been shown to react positively with β-galactosidase fusion proteins expressed by phage carrying DNA coding for the core protein of the mammary mucin. It appears therefore that at least part of each of the epitopes recognized by HMFG-1 and HMFG-2 contain amino acids but it must be assumed that some of these epitopes on the core protein are exposed, i.e. not masked in the fully glycosylated molecule. The HMFG-2 epitope is however less abundant on the milk mucin that the HMFG-1 epitope, while it is readily detectable on the mucin molecules expressed by tumours (1). These molecules have a smaller molecular weight and may be less heavily glycosylated or polymerized.

Here we have reported the development of new antibodies which are reactive with the protein core of the mucin and with the partially deglycosylated molecule, but which are unreactive with the fully processed mucin produced by the lactating mammary gland. One of these antibodies SM-3, which is an IgG1, has been studied in more detail. It has been shown to react with the mucin molecules which are produced by breast cancer cells and are recognised by many antibodies developed against the intact milk mucin. It should be emphasized however that the epitope recognised by SM-3 which is on the core protein and is exposed in the mucin as processed by tumour cells, is not exposed on the normally processed milk mucin. This feature offers the possibility of enhanced tumour specificity, and a pilot immunohistochemical study of breast tumours and tissues has shown that indeed the SM-3 antibody reacts strongly with the majority of primary breast cancers (91%) but shows little or no reaction with benign breast tumours, resting or lactating breast, and most normal tissue.

There are several implications of the work described here which may be important for both basic and clinical studies in breast cancer. The observation that parts of the core protein (detectable by antibodies) are exposed on the mucins as processed by breast cancer but masked on the mucin as processed by cells in normal breast and benign tumours implies that there is an alteration in the processing of the mucin in malignancy. A more detailed study of the processing of the mucin in normal and malignant cells may then give basic information for defining the malignant cell. Moreoever, since the specificity of the reaction of the antibody SM-3 for tumours is better than that of antibodies developed against the intact mucin, this antibody may prove to be a more effective diagnostic tool for the detection of breast cancer cells in tissue sections, tissue fluids and cells. The reactive components are membrane associated as well as intracellular and in vivo localisation of tumours may also be possible.

Abbreviations

The abbreviations used are: HMFG, human milk fat globule; PBS, phosphate-buffered saline (153 mM NaCl, 3 mM KCL, 10 mM $Na_2HPO_4$, 2 mM $KM_2PO_4$ pH 7.4); WGA, wheat germ agglutinin; PNA, peanut agglutinin; HPA, Helix pomatia agglutinin; BSA, bovine serum albumin; SDS, sodium dodecyl sulfate.

EXAMPLE 2

Purification and deglycosylation of human milk mucin was conducted as in Example 1 mucin was purified on an HMFG-1 antibody.

The stripped mucin preparations were separated by electrophoresis through $NaDodSO_4$/polyacrylamide gels (10%) and silver stained by two methods, one of which can be used to stain highly glycosylated proteins (22, 23).

Preparation of polyclonal rabbit antiserum to stripped core protein

One New Zealand White rabbit was immunized with 100 μg of the partially stripped core protein in complete Freund's adjuvant (Gibco). Booster injections of 500 μg of the totally stripped core protein were administered in incomplete Freund's adjuvant (Gibco ) 3 and 4 weeks after the initial injection and the rabbit was bled one week later. Ten microliters of immune serum (75 μg/ml protein) precipitated 200 ng of fully stripped core protein in a Protein A assay (24) and detected it on immunoblots. The immunoglobulin fractions of rabbit preimmune and rabbit anti-mucin core protein were prepared by adding ammonium sulfate to 50% saturation. The resulting pellot was resuspended in one-half the original serum volume of PBS and dialyzed against the same buffer. After dialysis, only residual precipitate was removed by centrifugation. Immunoglobin fractions were stored in aliquots at −20° C.

Description of MAbs used

In addition to the polyclonal antiserum used for initial screening, a cocktail of two MAbs, SM-3 and SM-4 (see Example 1) which recognise the mucin core protein (20) and HMFG-1 and HMFG-2 (1, 14) were used to screen the purified plaques, the β-galactosidase fusion proteins and for immunoprecipitations from in vitro translated proteins*. Other MAbs used were a monoclonal anti-β-galactosidase antibody (25) which was a gift from H. Durbin (ICRF, London), an anti-interferon antibody, ST254 (24), LE61, a keratin antibody (26) and M18 which recognizes a carbohydrate structure on the milk mucin (27).

* The MAbs SM-3 and SM-4 (SM refers to stripped mucin) show strong reactivity with the partially and fully stripped core protein but no reactivity with the fully glycosylated mucin (20).

In Vitro translation of proteins

RNA was isolated from the human breast cancer cell line MCF-7 using the guanidium isothiocyanate method of Chirgwin et al. (28) and poly(A)$^+$ RNA was purified by chromatography using oligo (dT)-cellulose (New England Bio Labs). The poly(A)$^+$ RNA was translated in a retinculocyte lysate system (Amersham) in the presence of [$^{35}$S] methionine (1000 Ci/mmole; 1 Ci=37 GBq, Amersham). Samples containing 5×10$^4$ acid insoluble cpm were precipitated in a protein A assay (24) using MAbs SM-3, SM-4, HMFG-1, HMFG-2 and a control antibody to human interferon. The antibody-selected proteins were then separated on a 10% $NaDodSO_4$/polyacrylamide gel, impregnated with Amplify (Amersham) and exposed to XAR-5 film (Kodak) at −70° C.

Antibody screening of λgt11 library and protein blotting

The λgt11 library used in this study was constructed from mRNA isolated from the human breast cancer cell line MCF-7 and was generously provided by Philippe Walter and Pierre Chambon (Strasbourg, France). The poly (A)$^+$ RNA used for the preparation of the randomly primed library was prepared from mRNA that sedimented faster than 28S rRNA and was enriched in estrogen receptor (29). The library was made essentially as described by Huynh et al. and Young and Davis (30–32) and contained approximately 1×10$^6$ recombinants per μg of RNA. Between 85% and 95% of the plaques contained inserts.

The phage library was plated onto bacterial strain Y1090 and grown for 3 hr. at 42° C. After isopropyl β-D-thiogalactoside (IPTG) induction and 3 hr of growth at 37° C., filters were prepared from each plate and screened with anti-mucin core protein antibody by the method of Young and Davis (32). The first antibody used in screening was the rabbit antiserum raised against the stripped core protein prepared as described above. Prior to use in screening, the antiserum was diluted 1:200 in PBS containing 1% bovine serum albumin (PBS/BSA). Preabsorption with Y1090 bacterial lysate was not found to be necessary. The nitrocellulose filters (Schleicher and Schuell) were blocked by incubation in PBS containing 5% BSA for 1 hr at room temperature with gentle agitation. The filters were incubated at room temperature overnight with a 1:200 dilution of antiserum in heat sealed plastic bags. The filters were washed 5×5 min in PBS/BSA, and bound antibody was detected by using horseradish peroxidase-conjugated sheep anti-rabbit antiserum (Dako) diluted 1:500 with PBS/BSA and incubated for 2 hr with the filters. The filters were washed 5×5 min in PBS/BSA and 1×10 min in PBS before color detection using 4-chloro-1-naphthol (1). Immunoreactive bacteriophage were picked and purified through two additional rounds of screening. Subsequently, bacteriophage inserts were subcloned into the EcoRI sites of pUC8 (33) producing the plasmid used most extensively, pMUC 10. The plasmids were maintained in DH1 cells.

To examine the β-galactosidase-cDNA fusion proteins for immunoreactivity, cell lysates were derived. Lysogens were prepared as described in Young and Davis (34). Cells were pelleted, suspended in Laemmli sample buffer (35) and separated by electrophoresis through $NaDodSO_4$/polyacrylamide gels (10%) and transferred onto nitrocellulose filters as described (1, 36). The filters were treated as above for antibody screening.

Northern Analysis

RNA was isolated from tissue culture cells and frozen tissues by the guanidinium isothiocyanate method of Chirgwin et al. (28). Total RNA (10 μg per lane) was denatured by heating at 55° C. for 1 hr in deionized glyoxal and fractionated by electrophoresis through a 1.3% glyoxal gel (38). The RNA was transferred to nitrocellulose (Schleicher and Schuell), prehybridized and hybridized as described by Thomas (34). Filters were washed down to 0.1X SSC with 0.1% SDS at 65° C. and exposed to XAR-5 film (Kodak) at −70° C. with intensifying screens.

Southern analysis

High molecular weight genomic DNA was prepared from white blood cells and cell lines (39, 40). These genomic DNAs (10 μg) were cleaved with restriction enzymes following the manufacturer's recommended conditions and fractioned through 0.6% and 0.7% agarose gels. Cloned plasmid DNA was cleaved and fractionated on 1.3% agarose. The gels were denatured, neutralized and transferred to nylon membranes (Biodyne) according to the manufacturer's instructions. The EcoR1 insert from pMUC10 was separated on a 1% low melting point agarose (Biorad) gel and labelled with [$\alpha$-$^{32}$P]dCTP by the method of random priming (41) and hybridized to filters at 42° C. Filters were washed down to 0.1X SSC with 0.1% SDS at 55° C. and exposed to XAR-5 film (Kodak) at −70° C. with intensifying screens.

Results

Purification and deglycosylation of mucin glycoprotein

Mucin glycoprotein reactive with the monoclonal antibody HMFG-1 was prepared from pooled human breast milk by using an HMFG-1 antibody affinity column, followed by molecular sieve chromatography on Sephadex G-75 in order to remove lower molecular weight components (FIG. 7, lane 1). In order to demonstrate the homogeneity of the purified molecule, amino acid analyses of four separate preparations were performed and revealed a fairly consistent composition with serine, threonine, proline, alanine and glycine accounting for 58% of the amino acids. Periodic acid silver stained gels revealed a diffuse band of greater than 400,000 daltons visible only when the gel was treated with periodic acid before the silver stain (FIG. 7, lane 2). No other lower molecular weight bands were visualized on the gel using the silver stain without prior treatment with periodic acid.

The purified material was subjected to treatment with hydrogen fluoride to remove the 0-linked sugars that are characteristic of mucin glycoproteins. Two different reaction conditions were used which resulted in a partially deglycosylated core protein (treated at 0° C. for 2 hr) and a fully deglycosylated core protein (treated at room temperature for 3 hr) as determined by iodinated lectin binding following separation by gel electrophoresis and transfer to nitrocellulose paper (20). the partially deglycosylated core protein was reactive with wheat germ agglutinin, peanut agglutinin and helix pommatia lectin (which recognizes the linkage sugar N-acetylgalactosamine) whereas the fully stripped protein showed no reactivity with any of these three lectins.

The hydrogen fluoride treated core protein was separated by electrophoresis through NaDodSO$_4$/polyacrylamide gels (10%) and silver stained. Silver staining revealed that the predominant component of the partially stripped mucin was a high molecular weight band of about 400 kd, although faint bands of lower molecular weight could also be observed (FIG. 8, lane 1). Since the high molecular weight material showed a somewhat increased mobility in the gel and reacted with the lectin recognising the linkage sugar, it can be assumed that some sugars had been removed. The fully stripped mucin consisted of two bands of about 68 kd and 72 kd (FIG. 8, lane 2).

Antibody reactive proteins produced by MCF-7 cells

The MCF-7 breast cancer cell line expresses large amounts of HMFG-1 and -2 reactive material on its cell surface (14) and was thus judged to be suitable source of mRNA for a cDNA library. Before proceeding to screen the MCF-7 library with the monoclonal antibodies, they were tested for their ability to precipitate a component from in vitro translation products produced from MCF-7 mRNA. Poly (A)$^+$ RNA from MCF-7 was prepared and translated in vitro. Proteins from the translation reaction were immunoprecipitated using the monoclonal antibodies HMFG-1, HMFG-2, SM-3 and SM-4 and displayed by polyacrylamide gel electrophoresis and fluorography (FIG. 9). Two proteins of about 68 kd and 92 kd were immunoprecipitated by SMA-3 (lane 2) and SM-4 (lane 1). It was also found that HMFG-1 (lane 4) and HMFG-2 (lane 3) immunoprecipitated these proteins; however, no bands in these areas were precipitated by an irrelevant monoclonal antibody to human interferon (lane 5). The fact that HMFG-1 and -2 immunoprecipitated these proteins was an unexpected finding as it was previously thought that these MAbs recognize carbohydrate determinants (1). However, we also found that HMFG-1 and -2 react very strongly with the fully stripped, iodinated core protein (20). These results together with the MAb reactions on the β- galactosidase fusion proteins (see below) confirm that the epitopes for HMFG-1 and -2 are, at least in part, protein in nature.

The abundance of the core protein mRNA in total cellular poly (A)$^+$ RNA was 4% as estimated by comparing the amount of ($^{35}$S)methionine present as immunoprecipitated protein to the amount of methionine incorporated into total protein during in vitro translation.

Screening of the cDNA library

The λgt11 cDNA library made from size selected MCF-7 mRNA (see Methods) was screened initially with the polyclonal antiserum made to the mucin core protein which had been stripped of its carbohydrate. Screening of 2×10$^6$ plaques resulting in 11 positive clones, 7 of which were taken successfully through two further rounds of plaque purification.

To demonstrate that the reactivity of phage clones with the antibody probes was due to antigenic determinants on the cDNA translation product, β-galactosidase fusion proteins were made from all 7 clones. The proteins were separated by electrophoresis, transferred to nitrocellulose paper and probed with a variety of antibodies to the stripped mucin, including the polyclonal antiserum which was used initially to select the clones and a cocktail of SM-3 and SM-4. In addition, HMFG-1 and HMFG-2, the two monoclonal antibodies which originally detected this differentiation and tumour-associated epithelial mucin (1, 14) were tested. All 7 clones yielded fusion proteins which were specifically recognized by the polyclonal antiserum, the monoclonal cocktail, and HMFG-2. HMFG-1 antibody reacted with 6 of the 7 fusion proteins and failed to recognize the protein from clone 9 which contains the smallest insert. In every case the strongest signal was given by the HMFG-2 antibody and this reaction is shown in FIG. 10. Monoclonal antibodies to keratins and to a carbohydrate epitope on this fully glycosylated mucin were used as controls and showed no reactivity A monoclonal antibody to β-galactosidase was a positive control and the band recognized correlated in every case with the band recognized by the specific antibodies. The sizes of the fusion proteins varied in proportion to the sizes of the cDNA inserts found in the bacteriophage.

Characteristics of cDNAs and RNA blot analysis

The inserts from the λ clones were designated pMUC3–10 (omitting pMUC5) and were subcloned into the vector pUC B for easier manipulation. The 7 clones were compared to each other for sequence homology. Each of the plasmids was digested with EcoRI and the insert separated on a 1.4% agarose gel. The largest cDNA insert from pMUC10 was used to probe the inserts and found to hybridize to all 6 inserts (FIG. 11). pMUC 7 was found to contain two inserts following digestion with EcoRI; however, only 1 of the inserts hybridized to the pMUC10 probe. The insert bands were not derived from phage DNA since the pMUC10 probe did not hybridize to Hind III-digested λ phage DNA As shown by agarose gel electrophoresis (FIG. 11), the inserts vary in size from about 200 to up to about 1800 bp. The largest insert from pMUC10 has been used as the hybridization probe in all subsequent experiments.

*Escherichia coli* strain XL-1 blue, containing plasmid pMUC10, was deposited under the Budapest Treaty, on Jan. 3, 1996, as accession NCIMB 40782, with the National Collections of Industrial and Marine Bacteria Ltd., 23 St. Machar Drive, Aberdeen AB2 1RY, Scotland, United Kingdom. Upon issuance of a U.S. patent, the deposited biological material will be irrevocably and without restriction of condition made available to the public. The release of the deposit does not constitute a license to practice the claimed invention.

Because the λMUC clones were identified only by antibody binding, we needed additional assurance that they were indeed coding for the breast epithelial mucin. To determine the authenticity of pMUC10, we correlated the presence of mRNA hybridizing to the clone with mucin expression in various cell lines. As shown in FIG. 12, the cDNA hybridized to two transcripts of 4.7 kb and 6.4 kb in the RNA from the breast cancer cell lines MCP-7 and T47D which were shown previously to express the HMFG-2 antigen (1,14). Significantly, the pMUC10 probe hybridized to transcripts of approximately the same size in RNA extracted from normal mammary epithelial cells cultured from milk (42). A third band of 5.7 kb can be seen in the RNA from these normal cells. In contrast, three human cell types that lack the mucin, breast fibroblasts, Daudi cells and HS578T, a carcinosarcoma line derived from breast tissue (43), showed no detectable pMUC10-related mRNA. The 6.4 kb band appears to be the most abundantly expressed. The presence of at least two sizes of mRNA from MCF-7 cells correlates with the immunoprecipitation of two proteins of (molecular weights 68 kd and 92 kd) from in vitro translated mRNA from MCF-7 cells. The normal mammary epithelial cells were derived from pooled milk samples and the additional transcript observed may be due to polymorphisms among individuals.

Genomic DNA blot hybridization and detection of a restriction fragment length polymorphism (RFLP)

Genomic DNA was prepared from a panel of ten individuals consisting of six unrelated individuals and a family of four, and from three cell lines. The DNAs which were digested with HinfI or EcoRI and blotted and hybridized to the radiolabelled pMUC10 insert, exhibit restriction fragment length polymorphisms. The restriction fragments from the ten individuals and three cell lines are shown in FIGS. 13A–13B. The pattern consists of either a single band or a doublet of sizes ranging from 3400 bp to 6200 bp in the HinfI digest (with the exception of the ZR75-1 DNA in lane 12, FIG. 13A which shows three bands) or from 8200 bp to 9500 bp in the EcoRI digest (FIG. 13B). There appears to be a continuous distribution of the fragment sizes which implies a high in vivo instability at the locus. The pattern of fragments observed in the family of four (lanes 1–4) suggests that these fragments are allelic. Preliminary studies of the DNA made from white blood cells of normal, related individuals indicate the existance of a number of independent alleles with an autosomal codominant mode of inheritance These studies will be the subject of a separate investigation.

Discussion

The cDNA clones described here which were obtained from the MCF-7 λgt11 library were selected using polyclonal and monoclonal antibodies prepared against a normal cellular product, the milk mucin in its deglycosylated form. This was done because it was easier to obtain large quantities of the mucin for stripping than to prepare similar quantities of immunologically related glycoproteins expressed by breast cancer cells (44). The fact that the antibodies did select for cDNA coding for nonglycosylated core protein molecules in MCF-7 cells, strongly suggests that the glycoproteins in these cells, which were originally detected by their reaction with antibodies to the milk mucin, contain the same core protein as this mucin. This is confirmed by the detection of mRNAs of approximately the same sizes in the normal and malignant cells, using one of the probes isolated from the MCF-7 library. We will therefore refer to the antibody reactive glycoproteins on breast cancer cells as mucins, bearing in mind that their processing may be different resulting in molecules of different molecular weights but with the same core protein as that of the milk mucin.

Seven clones were obtained from the MCF-7 library of which the largest was 1800 kb. This clone cross hybridized with the other 6 smaller clones. The β-galactosidase fusion proteins expressed by six of the cross-hybridizing lambda clones were reactive with the polyclonal antiserum directed against the mucin core protein as well as with four well-characterized monoclonal antibodies directed to various epitopes on the stripped core protein, SM-3, SM-4, HMFG-1 and HMFG-2 (14,20). The smallest lambda clone, λMUC9, produced a β-galactosidase fusion protein which reacted with three of the four monoclonal antibodies and with the polyclonal antiserum.

The surprising result that the extensively characterized HMFG-1 and HMFG-2 monoclonal antibodies reacted strongly with the lambda plaques and the fusion proteins and could immunoprecipitate proteins from in vitro translated mRNA provides strong evidence that these clones do indeed code for a portion of the mucin core protein. Although previous evidence such as resistance to fixation, boiling, treatment with dithiothreitol and $NaDodSO_4$ and the presence of multiple epitopes on the molecule suggested that these were carbohydrate (1), it has now been established that the epitopes of the HMFG-1 and HMFG-2 monoclonal antibodies are definitely protein in nature. Carbohydrate may be required to obtain the strongest binding, either as part of the epitope or by conferring some conformational change on the protein portion, but part of the antigenic determinant must consist of an amino acid sequence. Since these two MAbs are reactive with the fully glycosylated milk mucin as well as the stripped core protein, this data means that the intact molecule contains areas of naked peptide which contribute to the antigenic sites for these two antibodies.

Confirmatory evidence that pMUC10 codes for the mammary mucin core protein is provided by RNA blots. The relative abundance of mRNA in the breast cancer cell lines MCF-7, T47D, ZR-75-1 and in normal mammary epithelial cells corresponds to the antigen expression by these cells as measured by the binding of the HMFG-1 and HMFG-2 monoclonal antibodies. Cell types which are negative for antigen expression such as human fibroblasts, Daudi cells and HS578T, a carcinosarcoma line derived from breast (14), are negative in RNA blot hybridizations. A fortuituous observation made with the ZR-75-1 cells yielded indirect strong evidence that pMUC10 does indeed code for the mucin glycoprotein core protein. This cell line, which routinely expresses large amounts both of mRNA and antigen, yielded one preparation of RNA which was unexpectedly negative by blot hybridization. It was subsequently found that those particular ZR-75-1 cells from which the RNA had been made had lost the expression of the antigen as well as this time (as determined by reaction with HMFG-1 and 2). Different passage numbers of the ZR-75-1 cells were recovered and shown once again to express both antigen and message. The sizes of the messages, 4.7 kb and 6.4 kb, are quite large, since a 68 kd or 92 Kd protein would need only about 3 kb to code for the protein portions. This suggests that a large portion of the mRNA maybe untranslated. Efforts are underway to obtain a full-length clone.

Thus, the cDNA clones presented here represent a portion of the gene coding for the human mammary mucin which is expressed by differentiated breast tissue as well as by most breast cancers. The major proteins precipitated from in vitro translation products of RNA from MCP-7 cells by antibodies to the milk mucin core protein (68 Kd) have an apparent molecular weight of 68 Kd and 92 Kd. These proteins, produced by the breast cancer cell therefore share epitopes with the 68 Kd core protein of the milk mucin (20). Whether a similar 92 Kd protein is also produced by normal mammary epithelial cells, and is truncated or destroyed by HF treatment is not yet clear. MCF-7 cells biosynthetically labelled with 14C amino acids yield upon immunoprecipitation with HMFG-1 and HMFG-2 antibodies, two glycosylated proteins of 320 kd and 430 kd, and it is possible that each of these glycoproteins utilizes only one core protein of either 68 Kd or 92 Kd. Alternatively, each of the glycoproteins could contain both the 92 Kd and 68 Kd proteins either in different proportions or variably glycosylated. Further screening of the library may yield full length cDNAs coding for both sizes of the immunologically related core proteins. Since there appears to be only a single gene (based on Southern blot data obtained by using a partial cDNA probe), it is probable that the multiple messages arise by alternative RNA splicing and this would explain the fact that they contain common sequences. Although a core protein of 68 kd appears to be small to yield a fully glycosylated molecule of greater than 300 kd which contains 50% carbohydrate, there is evidence that such a structure for mucins is possible. Ovine submaxillary mucin has a reported molecular weight of $1 \times 10^6$ daltons (45), yet its protein core consists of 650 amino acids resulting in a molecule of 58 kd (45).

The mucins which are detected with HMFG-1 and HMFG-2 MAbs on immunoblots of tumours and breast cancer cell lines show variations in size from 80 kd to 40 kd in the molecular weights of the tumour mucin molecules (1,47). Using these same antibodies which detect high molecular weight mucins present in normal urine, a polymorphism has indeed been shown to be genetically determined (48). Although the very low molecular weight components are likely to represent precursor forms of the mucin which appears to be incompletely processed in many tumour cells (20), the variations in the higher molecular weight components are likely to be due to this genetic polymorphism. It was unclear, however, whether the structural basis of the polymorphism was due to the genetically determined protein or to the carbohydrate portion of the mucin. The detection of restriction fragment length polymorphisms in the Southern blotting experiments using the mucin probe suggest that the mucin polymorphism occurs at the level of the DNA which codes for the protein. Preliminary sequence data suggest that the basis for this polymorphism is a region of variable tandem repeats present in the protein coding sequences. This structural feature may be responsible for the generation of the many allelic restriction fragments at the mucin locus. We are presently investigating the basis of the mucin polymorphism by a Southern blot survey of DNA from white blood cells of normal, related individuals whose inheritance pattern of urinary mucins has been determined. In addition, we are examining DNA preparations made from the white blood cells and tumours, of individual breast cancer patients to determine if there is any discordance between genotype in the paired samples, since tenderly repeated DNA may provide an unstable site where recombination or amplification could occur.

The presence of mucins in the majority of carcinomas and their association with the differentiation of mammary epithelial cells makes it particularly important to identify regions involved in the tissue specific and developmental regulation of the gene. Moreover, the introduction of a functional mucin gene into cells should provide insights into the role of this molecule in breast epithelial differentiation and possible enable us to identify any alterations in the function or expression of the mucin which are related to malignant transformation in the human breast.

Abbreviations

The abbreviations are as follows: PBS, phosphate-buffered saline; MAb, monoclonal antibody; IPTG, isopropyl β-D-thiogalactoside; bp, base pair(s); Kb, kilobase(s).

TABLE 1

Amino acid composition of the human milk mucin - comparison with PAS-O

| Amino acid | HMFG-1 purified milk mucin | Extensively stripped milk mucin | PAS-O (Sarmiru & Iamauchi 1982) |
| --- | --- | --- | --- |
| Asp | 6.1 | 7.2 | 6.4 |
| Thr | 9.4 | 9.7 | 9.8 |
| Ser | 9.1 | 13.0 | 13.1 |
| Glz | 6.3 | 9.6 | 8.3 |
| Pro | 14.8 | 14.4 | 12.0 |
| Gly | 8.1 | 10.1 | 12.2 |
| Ala | 12.3 | 11.9 | 13.0 |
| Cys | Not analysed | Not analysed | 0.5 |
| Val | 6.0 | 6.3 | 5.3 |
| Met | 0.5 | 0.4 | 0.8 |
| Ile | 1.6 | 1.7 | 1.9 |
| Leu | 4.5 | 4.8 | 3.7 |
| Tyr | 2.0 | 0.9 | 1.6 |
| Phe | 2.0 | 1.6 | 1.7 |
| His | 3.2 | 2.3 | 3.8 |
| Lys | 2.8 | 3.3 | 2.2 |
| Arg | 4.0 | 4.0 | 3.9 |

TABLE 2

Reactivity of the antibodies on intact, partially and totally deglycosylated milk mucin

| Antibody | $^{125}I$ cpm bound | | |
|---|---|---|---|
| | Intact molecule | Partially stripped mucin | Totally stripped mucin |
| 5.17 | 8,524 | 11,925 | 5,780 |
| 9.13 | 525 | 3,000 | 3,328 |
| SM-3 | 465 | 15,414 | 9,200 |
| SM-4 | 816 | 16,750 | 9,561 |
| HMFG-1 | 32,000 | 33,768 | 9,494 |
| HMFG-2 | 29,500 | 29,230 | 15,832 |
| NS2 medium | 397 | 845 | 650 |

The binding of the antibodies to iodinated intact, partially and totally deglycosylated milk mucin was assayed using the protein A plate method as described in Materials and Methods.

REFERENCES

1. Burchell, J. M., Durbin, H. and Taylor-Papadimitrious, U. (1983) J. Immunol. 131, 508–513.

2. Bramwell, M. E., Ehavanandan, V. P., Wiseman, G. and Harris, H. (1983) Br. J. Cancer 48, 177–183.

3. McIlhinney, R. A., Pratel, S. and Gore, M. E. (1985) Biochem. U. 227, 155–162.

4. Hilkens, J., Buijs, F., Hilgers, J., Hagemann, Ph., Calafat, J., Sonnenberg, A. and Van der Valk, M. (1984) Int. J. Cancer 34, 197–206.

5. Tagliabue, E., Porro, G., Barbanti, P., Della-Torre, G., Menard, S., Rilke, F., Cerasoli, S. and Colnaghi, M. (1986) Hybridoma 5, 107–115.

6. Johnson, V. G., Schlom, J., Paterson, A. J., Bennett, J., Magnani, J. L. and Colcher, D. (1986) Cancer Res. 46, 850–857.

7. Sekine, H., Ohno, T. and Kufe, D. W. (1985) J. Immunol. 135, 3610–3615.

8. Ormerod, M. G., Steele, K., Edwards, P. A. W. and Taylor-Papadimitriou, J. (1984) J. Expt. Path. 1, 263–271.

9. Wilkinson, M. J., Howell, A., Harris, J., Taylor-Papadimitriou, J., Swindell, R. and Sellwood, R. A. (1984) Int. J. Cancer 33, 299–304.

10. Kufe, D., Inghirami, G., Abe, M., Hayes, D., Justi-Wheeler, H. and Schlom, J. (1984) Hybridoma 3, 223–232.

11. Price, M. R., Edwards, S., Robins, R. A., Hilgens, J., Hilkens, J. and Baldwin, R. (1986) Eur. J. Can. Clin. Oncol. 22, 115–117.

12. Johnston, W. W., Szpak, C. A., Lottick, S. C., Thor, A. and Schlom, J. (1985) Cancer Res. 45, 1984–1900.

13. Rasmussen, B. B., Pedersen, B. V., Thorpe, S. M., Hilkens, J., Hilgers, J. and Rose, C. (1986) Cancer Res. 45, 1424–1427.

14. Taylor-Papadimitriou, J., Peterson, J. A., Arklie, J., Burchell, J., Ceriani, R. L. and Bodmer, W. F. (1981) Int. J. Cancer 28, 17–21.

15. Burchell, J., Wang, D. and Taylor-Papadimitriou, J. (1984) Int. J. Cancer 34, 763–768.

16. Shimizu, M. and Yamauchi, K. (1982) J. Biochem. 91, 515–519.

17. Ormerod, M. G., Steele, K., Westwood, J. H. and Mazzini, M. N. (1983) Br. J. Cancer 48, 533–541.

18. Taylor-Papadimitriou, J., Lane, E. G. and Chang, S. E. (1983) In, Understanding Breast Cancer: Clinical and Laboratory Concepts. (Rich, M. A., Hager, J. C. and Purmanaki, P. Eds.) Marcel Dekker, Inc. New York and Basel, pp. 215–246.

19. Chang, S. E. and Taylor-Papadimitriou, J. (1983) Cell Diff. 12, 143–154.

20. Example 1 above.

21. Mort, A. and Lamport, D. (1977) *Anal. Biochem.* 82, 289–309.

22. Wray, W., Boulikas, T., Wray, K. P. and Hancock, R. (1981) Anal. Biochem. 118, 197–203.

23. Dubray, G. and Bezard, G. (1982) Anal. Biochem. 119, 325–329.

24. Shearer, M., Taylor-Papadimitriou, J., Griffin, D. and Balkvill, F. (1984) J. Immunol. 133, 3096–3101.

25. Durbin, H. and Bodmer, W. F. (1986) J. Immunol. Meth., In Press.

26. Lane, E. B. (1982) J. Cell Biol. 92, 665–673.

27. Gooi, H. C., Jones, N. J., Housell, E. F., Scudder, P., Hilkens, J., Hilgers, J. and Peizi, T. (1985) Biochem. Biophys. Res. Commun. 131, 543–550.

28. Chirgwin, J. M., Przybyla, A. E., McDonald, R. J. and Rutter, W. J. (1979) Biochem. 18, 5194–5199.

29. Walter, P., Green, S., Green, G., Krust, A., Bornert, J. M., Heltsch. J. M., Staub, A., Jensen, E., Scrace, G., Waterfield, M. and Chambon, P. (1985) Proc. Natl. Acad. Sci. USA. 82, 7889–7893.

30. Huynh, T. V., Young, R. A. and Davis, R. W. (1985) In, DNA Cloning: A Practical Approach, ed. Glover, D. M. (IRL, Oxford), Vol. 1, pp. 98–121.

31. Young, R. A. and Davis, R. W. (1983) Proc. Natl. Acad. Sci. USA 80, 1194–1198.

32. Young, R. A. and Davis, R. W. (1983) Science 222, 778–782.

33. Vieira, J. and Messing, J. (1982) Gene 19, 259–268.

34. Young, R. A. and Davis, R. W. (1985) In Genetic Engineering, eds. Setlow, J. K. and Hollaender, A. (Plenum, New York), Vol. 7.

35. Laemmli, U. K. (1970) Nature (Lond) 227, 680–685.

36. Towbin, H., Staehelin, Y. and Gordon, J. (1979) Proc. Natl. Acad. Sci. USA. 76, 4350–4354.

37. Maniatis, T., Fritsch, E. F. and Sambrook, J. (1982) Molecular Cloning: A Laboratory Manual (Coldspring Harbor Laboratory, Cold Spring Harbor, N.Y.).

38. Thomas, P. A. (1980) Proc. Natl. Acad. Sci. USA. 77, 5201–5205.

39. Woodhead, J. L., Fallon, R., Figuieredo, H., Langdale, J. and Malcolm, A. D. B. (1986) In Human Genetic Diseases, ed. Davies, K. E. (IRL, Oxford), p. 56.

40. Old, J. M. (1986) In Human Genetic Diseases, Ed. Davies, K. E., (IRL, Oxford), p. 4.

41. Feinberg, A. P. and Vogelstein, B. (1984) Anal. Biochem. 137, 266–267.

42. Taylor-Papadimitriou, J., Purkis, P. and Fentiman, I. S. (1980) J. Cell. Physiol. 102, 317–321.

43. Hackett, A. J., Smith, H. S., Springer, E. L., Owens, R. B., Nelson-Rees, W. A., Riggs, J. L. and Gardner, M. B. (1977) J. Natl. Cancer Inst. 58, 1795–1800.

44. Griffiths, A. B., Burchell, J., Taylor-Papadimitriou, J., Gendler, S. J., Lewis, A. and Tilly, R. (1987) Int. J. Cancer (submitted).

45. Gottschalk, A., Bhargava, S. and Mary, V. In Gottschalk, A. (ed) Glycoproteins their composition, structure and function, pp. 810–829, Elsevier, N.Y.

46. Hill, M. D. Jr., Reynolds, J. A. and Hill, R. (1977) J. Biol. Chem. 252, 3791–3798.

47. Taylor-Papadimitriou, J., Millis, R., Burchell, J., Nash, R., Pang, L. and Gilbert, J. (1985) J. Expt. Path. 2, 247–260.

48. Swallow, D., Griffiths, B., Bramwell, M., Wiseman, G. and Burchell, J. (1986) Disease Markers 3, In Press.

49. Abe, M. and Xufe, D. Effects of maturational agents on expression and secretion of two partially characterized high molecular weight milk-related glycoproteins in MCF-7 breast carcinoma cells. J. Cell. Physiol. 126:126–136, 1986.

50. Arklie, J., Taylor-Papadimitriu, J., Bodmer, W. F., Egan, M. and Millis, R. Differentiation antigens expressed by epithelial cells in the lactating breast are also detectable in breast cancers. Int. J. Cancer 28:23–29, 1981.

51. Bolton, A. I. and Hunter, W. M. The labelling of proteins to high specific radioactivities by conjugation to a $^{125}$I containing acylating agent. Biochem. J. 133:529–538, 1973.

52. Karlsson, S., Swallow, D., Griffiths, B., Corney, G. and Hoplinson, P. A genetic polymorphism of a human urinary mucin. Ann. Hum. Genet. 47:253–269, 1983.

53. Kearney, J. F., Radbruch, A., Liesegang, B. and Rajowsky, K. A new mouse myeloma cell line that has lost immunoglobulin expression but permits the construction of antibody-secreting hybrid cell lines. J. Immunol. 123:1548–1550, 1979.

54. Melero, J. and Gonzalez-Rodriguez, J. Preparation of monoclonal antibodies against glycoproteins 111a *of human platelets. Eur. J. Biochem.* 141:421–427, 1984.

55. Clamp, J. R., Allen, A., Gibbons, R. A. and Roberts, G. Chemical aspects of mucins. Br. Med. Bull. 34: 25–41, 1978.

What is claimed is:

1. A non-naturally occurring antigen selected from the group consisting of
   (a) an immunogen comprising (i) a portion, at least five consecutive amino acids in length, of a tandem repeat sequence of the core protein of a human polymorphic epithelial mucin, said portion comprising an epitope of said core protein recognized by monoclonal antibody SM-3, secreted by hybridoma cell line HSM3 (accession number ECACC 87010701), and (ii) an immunogenic carrier, said immunogen also being recognized by SM-3,
   said portion (i) and said immunogenic carrier (ii) being covalently linked, directly or indirectly, so as to form said immunogen and
   (b) an antigenic fragment of the core protein of a human polymorphic epithelial mucin which fragment comprises at least five consecutive amino acids of a tandem repeat sequence of the core protein of a human polymorphic epithelial mucin, said fragment comprising an epitope of said core protein recognized by monoclonal antibody SM-3, said fragment also being recognized by SM-3,
   where said antigen does not occur in nature in normal or tumor cells, and
   where said antigen differs in amino acid sequence or glycosylation pattern from glycoproteins produced by normal and malignant human mammary epithelial cells and recognized by the monoclonal antibody HMFG-1.

2. The antigen of claim 1 which is the antigen of (a) above.

3. The antigen of claim 1 which is the fragment of (b) above.

4. The antigen of claim 1 which is a fusion protein.

5. The antigen of claim 1 wherein the mucin, and messenger RNA encoding its core protein, are obtainable from the human cancer cell line MCF7, and the messenger RNA specifically hybridizes, under hybridizing conditions of 0.1× SSC, 0.1% SDS at 65° C., to I) the DNA sequence

```
5'                                          *
ACC GTG GGC TGG GGG GGC GGT GGA GCC CGG-

GGC CGG CCT GGT GTC CGG GGC CGA GGT GAC-
                    *
ACC GTG GGC TGG GGG GGC GGT GGA GCC CGG-
                                         3'
GGC CGG CCT GGT GTC CGG GGC CGA GGT GAC, or
```

II) DNA complementary to the DNA of a), i.e. of sequence

```
5'
GTC ACC TCG GCC CCG GAC ACC AGG CCG GCC-
  *
CCG GGC TCC ACC GCC CCC CCA GCC CAC GGT-

GTC ACC TCG GCC CCG GAC ACC AGG CCG GCC-
  *                                     3'
CCG GGC TCC ACC GCC CCC CCA GCC CAC GGT,
``` with each base with an asterisk immediately above it being omitted.

6. The antigen of claim 5 which is the antigen of (a) above.

7. The antigen of claim 5 which is the fragment of (b) above.

8. The antigen of claim 5 wherein the portion of said immunogen, or said fragment, is encoded, in one of the possible reading frames, by a contiguous portion of a DNA sequence complementary to the reference DNA sequence 5' CGT GGG CTG GGG GGG
   CGG TGG AGC CGG GGC
   CGG CCT GGT GTC CGG
   GGC CGA GGT GAC AC 3'.

9. The antigen of claim 1, wherein the mucin, and messenger RNA encoding its core protein, are obtainable from the human cancer cell line MCF7, the messenger RNA specifically hybridizes, under hybridizing conditions of 0.1× SSC, 0.1% SDS at 65° C., to the MCF7-derived insert of clone pUMC10, deposited as NCIMB 40782, and the epitope is encoded by a portion of the MCF7-derived insert of clone pMUC10.

10. The antigen of claim 1 wherein said portion or fragment is at least ten consecutive amino acids in length.

11. The antigen of claim 1 in which the antigen comprises an entire tandem repeat sequence of said core protein.

12. The antigen of claim 1 in which the antigen comprises at least two tandem repeat sequences of said core protein.

13. The antigen of claim 1 in which the antigen comprises at least three tandem repeat sequences of said core protein.

14. The antigen of claim 1 in which the carrier is a protein.

15. The antigen of claim 14 in which the carrier is keyhole limpet hemo cyanin, albumin or thyroglobulin.

16. The antigen of claim 1 which is not glycosylated.

17. The antigen of claim 1 which does not comprise the entire tandem repeat sequence.

18. The antigen of claim 1 which is an immunogen consisting essentially only of said epitope and said immunogenic carrier, the latter being foreign to said mucin.

19. The antigen of claim 1 which is a fragment consisting essentially only of said epitope.

20. The antigen of claim 1 which is a polypeptide modified by addition of N-acetyl galactosamine on serine and/or threonine residues or by addition of oligosaccharide moieties to that or via other linkage sugars.

21. The antigen of claim 1 which comprises 5 or more consecutive residues of the tandem repeat sequence (I) Val Thr Ser Ala Pro Asp Thr Arg Pro Ala Pro Gly Ser Thr Ala Pro Pro Ala His Gly Val Thr Ser Ala Pro Asp Thr Arg Pro Ala Pro Gly Ser Thr Ala Pro Pro Ala His Glu.

22. A protein derivable from the human polymorphic epithelial mucin, said protein being
(a) recognized by monoclonal antibody SM-3, secreted by hybridoma cell line HSM3 (accession number ECACC 87010701),
(b) unrecognized by peanut lectin (PNA), wheat germ agglutinin (WGA), and Helix pomatia agglutinin (HPA), and
(c) obtainable by (i) treating the human polymorphic epithelial mucin with anhydrous hydrogen fluoride for 3 hours at room temperature, or (ii) expressing a DNA sequence encoding the protein component of the human polyphorphic epithelial mucin in cells incapable of glycosylating said protein component,
and in at least partially purified form.

23. The protein of claim 22, said protein being obtained by stripping carbohydrate from the native mucin.

24. The protein of claim 22, said protein being obtained by expression in cells incapable of glycosylation of proteins.

25. The protein of claim 22 which is obtainable by expressing a gene encoding the protein component of the human polyphorphic epithelial mucin in cells incapable of glycosylating said protein component.

26. A non-naturally occurring polypeptide which is specifically recognized by SM-3 and which comprises 5 or more consecutive residues within the sequence (I) Val Thr Ser Ala Pro Asp Thr Arg Pro Ala Pro Gly Ser Thr Ala Pro Pro Ala His Gly Val Thr Ser Ala Pro Asp Thr Arg Pro Ala Pro Gly Ser Thr Ala Pro Pro Ala His Glu,
said polypeptide being free of carbohydrate.

27. The polypeptide of claim 26 which comprises ten or more consecutive residues within sequence (I).

28. A non-naturally occurring antigen selected from the group consisting of
(a) an immunogen comprising (i) a portion, at least five consecutive amino acids in length, of a tandem repeat sequence of the core protein of a human polymorphic epithelial mucin, said portion comprising an epitope of said core protein recognized by monoclonal antibody SM-3, secreted by hybridoma cell line HSM3 (accession number ECACC 87010701), and (ii) an immunogenic carrier, said immunogen also being recognized by SM-3,
said portion (i) and said immunogenic carrier (ii) being covalently linked, directly or indirectly, so as to form said immunogen and
(b) an antigenic fragment of the core protein of a human polymorphic epithelial mucin which fragment comprises at least five consecutive amino acids of a tandem repeat sequence of the core protein of a human polymorphic epithelial mucin, said fragment comprising an epitope of said core protein recognized by monoclonal antibody SM-3, said fragment also being recognized by SM-3,
where said antigen does not occur in nature in normal or tumor cells.

29. The antigen of claim 28 where said immunogen differs in amino acid sequence or glycosylation pattern from glycoproteins produced by normal and malignant human mammary epithelial cells.

30. In a method of immunization, wherein an immunogen is used to immunize a human or animal subject, the improvement wherein the immunogen is, the antigen of claim 1.

31. The method of claim 30 in which the antigen is the fragment of (b) above.

32. The method of claim 30 in which the antigen is the fragment of (a) above.

* * * * *